United States Patent
Campos Uribe et al.

(10) Patent No.: US 11,752,325 B2
(45) Date of Patent: Sep. 12, 2023

(54) FUNCTIONAL ELECTRICAL STIMULATION SYSTEM OFFERING COORDINATED AND NATURAL MOVEMENTS

(71) Applicant: BIOMEDICAL DEVICES SPA, Santiago (CL)

(72) Inventors: Luis Osvaldo Campos Uribe, Nunoa Santiago (CL); Moises Aaron Campos Uribe, Huechuraba Santiago (CL); Sebastian Osvaldo Mardones Mardones, Santiago (CL); Mattia Ignazio Rigotti Thompson, Las Condes Santiago (CL); Matias Felipe Hosiasson Retamal, La Reina Santiago (CL)

(73) Assignee: BIOMEDICAL DEVICES SPA, Santiago (CL)

( * ) Notice: Subject to any disclaimer, the term of this patent is extended or adjusted under 35 U.S.C. 154(b) by 177 days.

(21) Appl. No.: 15/734,800

(22) PCT Filed: Jul. 10, 2019

(86) PCT No.: PCT/IB2019/055894
§ 371 (c)(1),
(2) Date: Dec. 3, 2020

(87) PCT Pub. No.: WO2020/012389
PCT Pub. Date: Jan. 16, 2020

(65) Prior Publication Data
US 2021/0228862 A1    Jul. 29, 2021

(30) Foreign Application Priority Data
Jul. 12, 2018   (CL) .................................. 1900-2018

(51) Int. Cl.
| | | |
|---|---|---|
| *A61N 1/04* | (2006.01) | |
| *A61N 1/36* | (2006.01) | |
| *G16H 20/30* | (2018.01) | |
| *A63B 22/06* | (2006.01) | |

(52) U.S. Cl.
CPC ....... *A61N 1/0452* (2013.01); *A61N 1/36003* (2013.01); *A61N 1/36031* (2017.08);
(Continued)

(58) Field of Classification Search
CPC .......................... A61N 1/0452; A61N 1/36031
(Continued)

(56) References Cited

U.S. PATENT DOCUMENTS

| | | | | |
|---|---|---|---|---|
| 7,079,899 B2 * | 7/2006 | Petrofsky | ............... | A61N 1/326 607/50 |
| 8,165,668 B2 * | 4/2012 | Dacey, Jr. | ................ | A61B 5/24 607/46 |

(Continued)

FOREIGN PATENT DOCUMENTS

| | | | | |
|---|---|---|---|---|
| WO | 2011079866 A1 | 7/2011 | | |
| WO | WO-2011079866 A1 * | 7/2011 | ........... | A61N 1/0456 |

(Continued)

OTHER PUBLICATIONS

International Search Report and Written Opinion for Corresponding International Application No. PCT/B2019/055894 (12 Pages) (Jul. 14, 2020).

*Primary Examiner* — Carl H Layno
*Assistant Examiner* — Manolis Pahakis
(74) *Attorney, Agent, or Firm* — LUCAS & MERCANTI, LLP

(57) ABSTRACT

A functional electrical stimulation system and method is provided, offering coordinated and natural movements for people or animals with motor system damage, which includes: at least one electrical stimulation device delivering (Continued)

electrostimulation signal to form dynamic stimulation curves through at least one stimulation channel by electrodes, at least one main processor, which communicates with a communication unit, with a high voltage generator and with a current controller, at least one sensing device bi-directionally connected to the electrical stimulation device, the sensing device processes and transmits the information to predictively stimulate according to the user needs, and a computational device bi-directionally connected to the electrical stimulation device having computational device with a display screen, a configuration unit and a communication unit allowing information exchange with the electrical stimulation device.

21 Claims, 17 Drawing Sheets

(52) U.S. Cl.
 CPC .......... *A61N 1/36034* (2017.08); *A63B 22/06* (2013.01); *G16H 20/30* (2018.01); *A63B 2220/12* (2013.01); *A63B 2220/73* (2013.01); *A63B 2230/062* (2013.01); *A63B 2230/50* (2013.01)

(58) Field of Classification Search
 USPC .......................................................... 607/84
 See application file for complete search history.

(56) References Cited

U.S. PATENT DOCUMENTS

| | | | | |
|---|---|---|---|---|
| 8,354,881 B2* | 1/2013 | Denison | ............... | A61B 5/7217 330/10 |
| 8,419,804 B2* | 4/2013 | Herr | ......................... | A61H 3/00 623/24 |
| 8,880,178 B2* | 11/2014 | Popovic | ............. | A61N 1/36003 607/148 |
| 9,072,887 B2* | 7/2015 | Kagan | .................. | A61N 1/0529 |
| 10,512,774 B2* | 12/2019 | Dixon | ...................... | A61H 3/00 |
| 10,953,225 B2* | 3/2021 | Druke | .................. | A61N 1/0492 |
| 11,229,789 B2* | 1/2022 | Spurling | .............. | A61N 1/0452 |
| 2002/0183802 A1* | 12/2002 | Fang | .................. | A61N 1/36107 607/48 |
| 2007/0038066 A1* | 2/2007 | Sun | .......................... | A61B 5/05 600/407 |
| 2008/0061630 A1* | 3/2008 | Andreu | .............. | A61N 1/36003 307/104 |
| 2008/0079444 A1* | 4/2008 | Denison | ................... | G01D 5/24 324/679 |
| 2009/0030344 A1* | 1/2009 | Moser | ....................... | A61F 2/70 600/587 |
| 2012/0143568 A1* | 6/2012 | Kagan | ................ | A61N 1/36082 257/253 |
| 2014/0039571 A1* | 2/2014 | Wolpaw | ................. | A61B 5/742 607/45 |
| 2016/0367813 A1* | 12/2016 | Pepin | ................. | A61N 1/36125 |
| 2017/0001003 A1* | 1/2017 | Pivonka | .................. | A61B 5/4836 |
| 2019/0200891 A1* | 7/2019 | Jung | ...................... | A61B 5/296 |
| 2019/0247650 A1* | 8/2019 | Tran | ...................... | A61N 1/3704 |
| 2019/0336763 A1* | 11/2019 | Spurling | ............. | A61N 1/0456 |

FOREIGN PATENT DOCUMENTS

| | | |
|---|---|---|
| WO | 2015148184 A1 | 10/2015 |
| WO | 2015188889 A1 | 12/2015 |
| WO | 2018098046 A2 | 5/2018 |
| WO | 2020012389 A2 | 1/2020 |

* cited by examiner

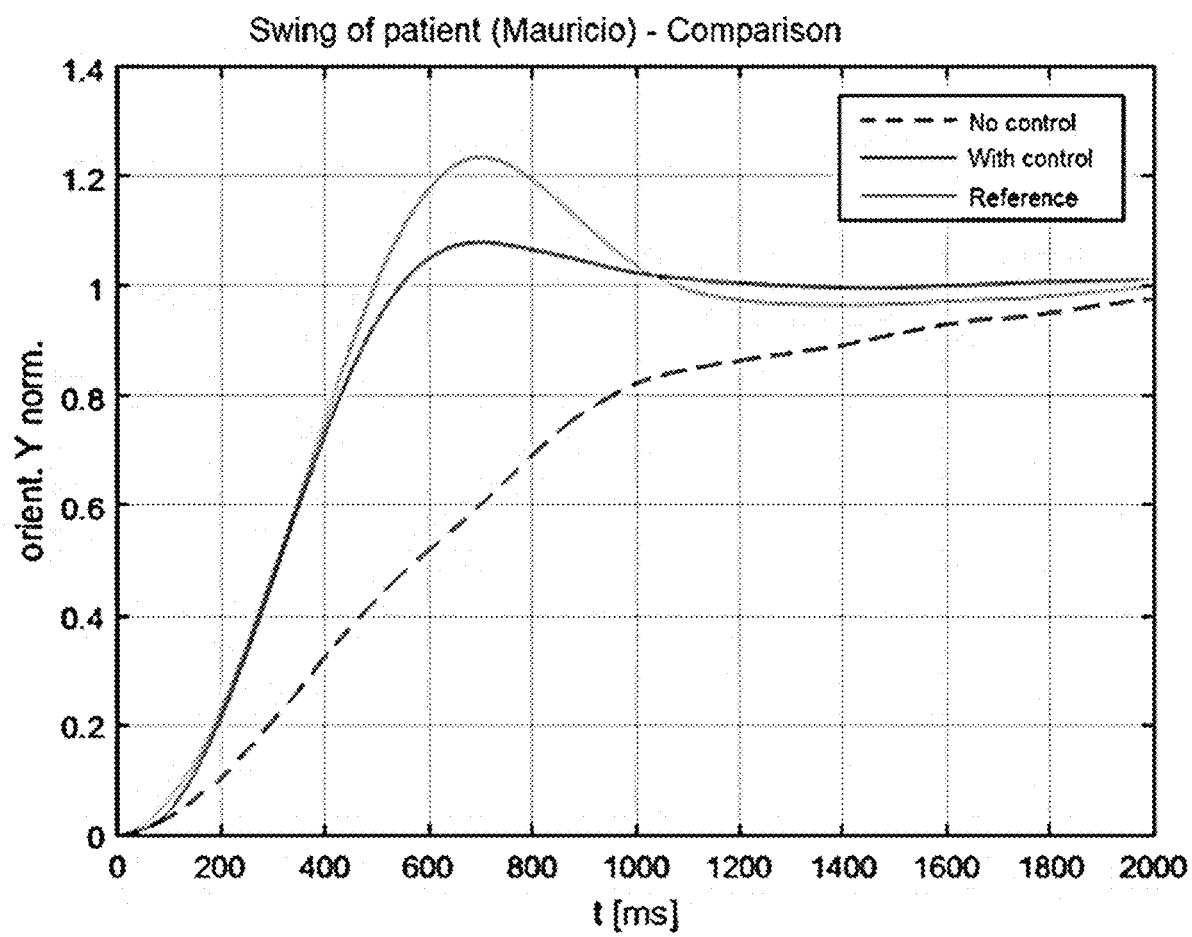
Fig. 3 d) (cont'd)

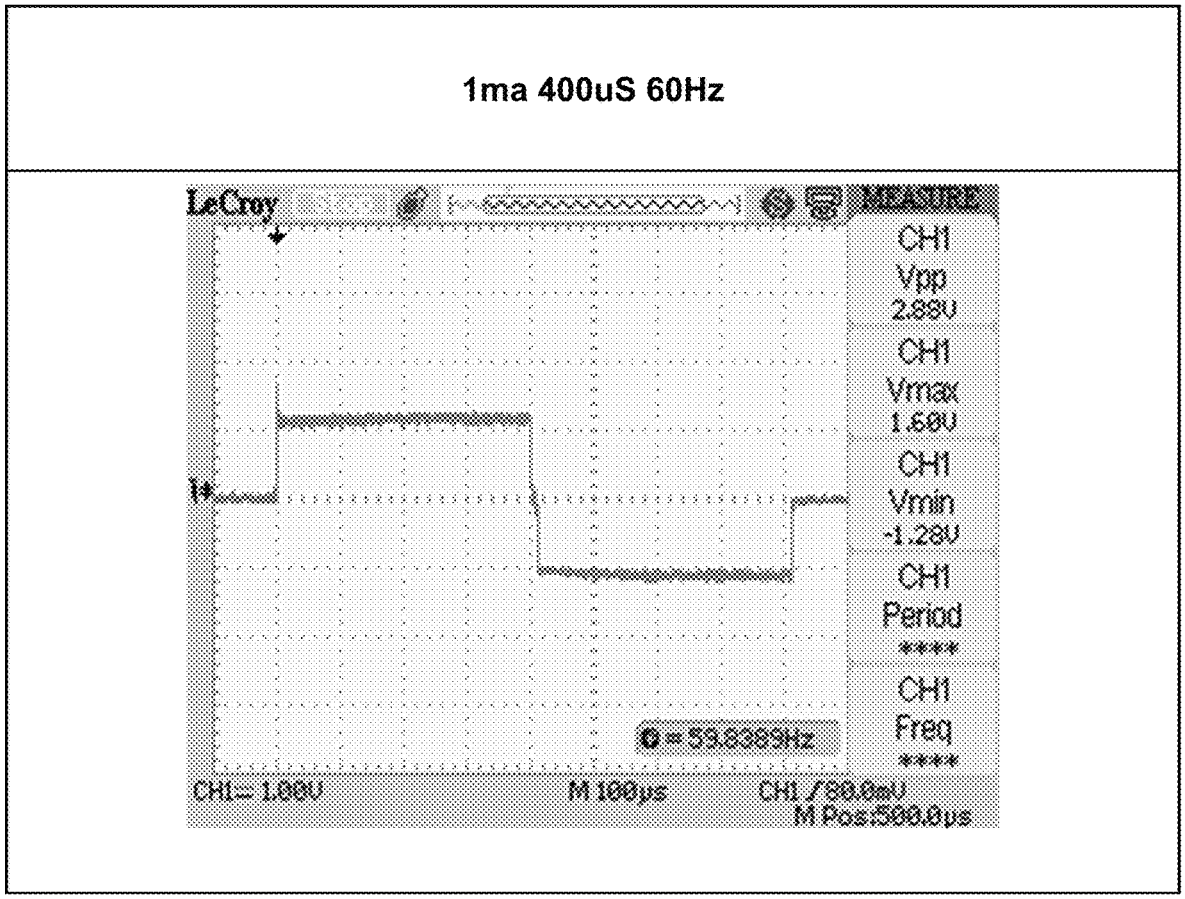
Fig. 7 a) (cont'd)

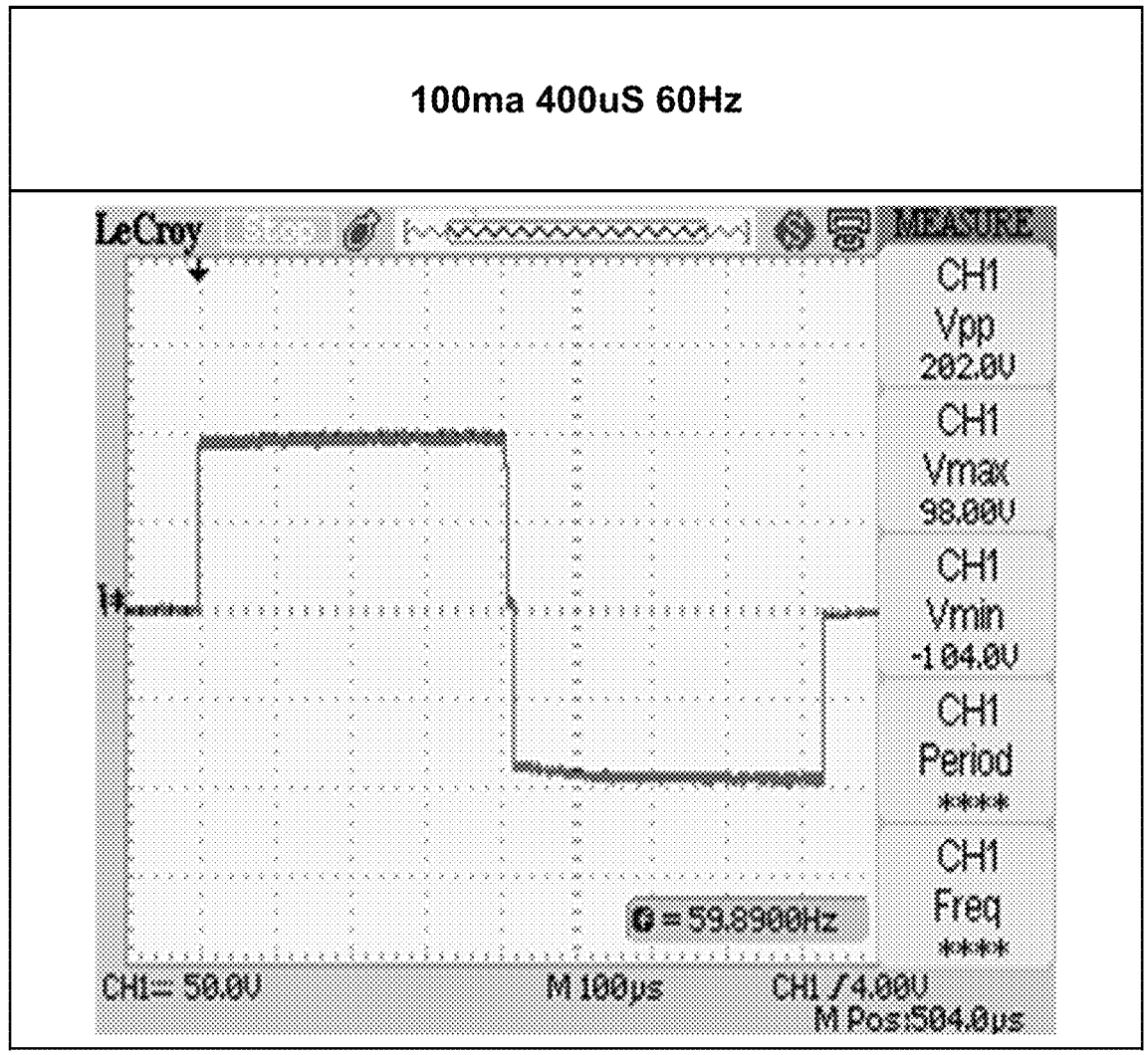
Fig. 7 a) (cont'd)

FUNCTIONAL ELECTRICAL STIMULATION SYSTEM OFFERING COORDINATED AND NATURAL MOVEMENTS

CROSS REFERENCE TO RELATED APPLICATION

This Application is a 371 of PCT/IB2019/055894 filed on Jul. 10, 2019, which, in turn, claimed the priority of Chilean Patent Application No. 1900-2018 filed on Jul. 12, 2018, both applications are incorporated herein by reference.

FIELD OF THE INVENTION

The present invention relates to the industry of systems and methods for functional electrostimulation (FES in short), for individuals or animals with some form of disability in their movements.

In particular, the present invention relates to a system and a method that improves the lack of functional electrostimulation system for daily use allowing coordinated and natural movement in individuals or animals with damages to their motor system.

Functional electrostimulation maximizes rehabilitation in this type of individuals or animal. It provides a 130% relative increase in the cross section area of muscles such as quadriceps as compared to people who do not use it. This results in an increase of over 1000% in the muscular strength of a user, since it is common for them to lose most of their muscular mass without treatment. In addition, it allows the performance of functional exercises providing not only physical, but also neurological benefits to the users, whilst taking advantage of the brain's neuroplasticity to relearn motor functions.

Electrostimulation decreases secondary diseases generated by the lack of movement and increases quality of life. These secondary diseases are extremely common. For people suffering from a spinal injury, thrombosis represents 10% of deaths during the first year. These people have an average of 2.5 infections per year, each of which can be fatal. The risk of osteoporosis increases, since they lose 50% of the bone mass in the affected limbs in the first 12 months.

The present invention optimizes the cost required from the health system since it allows the use of functional electrostimulation in "homecare" applications. This allows to maximize the quantity of therapy for each user without having to incur in further costs for care in specialized centers, hospitals or clinics. It also decreases the required time. Functional results using the invention are seen in a span of less than 6 months. This compared to results that take more than 2 years with conventional therapy (without electrostimulation) and that usually do not get completed, given its lengthy duration.

HISTORICAL BACKGROUND

Functional electrostimulation has been in existence for more than 50 years. It has been proven to produce the best results in terms of rehabilitation for individuals with paralysis, currently representing 2% of the world's population. In the United States, for instance, every year there are eight hundred thousand new cases of cerebrovascular accidents/ strokes. Although the application of electrostimulation in patients with paralysis is not new, it is necessary to devise new solutions using technology in order to meet the demand at a global level. Nowadays only 12% of individuals with paralysis have access to some type of rehabilitation, which most of the time does not include electrostimulation.

In the case of Canada, most therapists are aware of the benefits of FES treatments and 52% acknowledge that they should increase their use, yet less than 15% of therapists use the technology since it is very difficult and expensive to include it in their therapies. It is to be expected that the use of FES in less developed countries would be lower or even non-existent, for instance: Chile, Argentina and other countries of Latin America.

The types of paralysis are very diverse. Some of the most common cases are: paraplegia, tetraplegia, hemiplegia, foot drop, among others. These paralyzes can in turn be caused by multiple reasons: stroke (CVA), spinal cord injury (SCI), Traumatic brain injury (TBI), amyotrophic lateral sclerosis (ALS), etc. The healthcare system needs a tool enabling it to meet these diverse needs in a cost-effective way.

There is no system today allowing the production of functional exercises in all stages of rehabilitation for a person suffering from any of these types of paralysis. Current systems are generally designed to be used with a single piece of equipment (bicycle, partial weight bearing, rowing) and do not allow its use throughout multiple applications, motor exercise and therapies. This makes the application of therapies that must evolve along difficult, as the patient's control and strength improves during their rehabilitation.

On the other hand, current solutions do not use technology to its full potential. There is no system that really adapts and adjusts to what the user needs at each moment to achieve coordinated and natural movements in the patient. Many of the current solutions carry the concepts of binary activation, a technology used at a time when activation only by switches was possible.

It is important to take advantage of the users' rehabilitation potential to the fullest, in all stages, since this can mean the difference between being able to walk again or not. It is common for patients and therapists to disregard the use of state-of-the-art technologies due to their complexity for the user and their lack of versatility for use through all stages of rehabilitation.

STATE OF ART

It is necessary to facilitate rehabilitation to individuals with paralysis, in all its stages, through FES systems. In the state of the art, several solutions have been found partially solving the posed technical problem. Among what is published, patent application WO2011/079866A1 discloses an electrostimulation system that uses a system of multiple electrodes and pressure sensors to apply voltage-based pulses. This document however does not disclose a system allowing the optimal use of the stimulation based on feedback stimulation curves, since it does not use an optimal control method in terms of the necessary stimulation, focusing instead on the correct positioning of the stimulation only, positioning that can be achieved with repositionable electrodes instead of using a matrix of tens of fixed electrodes. The control described in the aforementioned patent is deficient. On the one hand, it uses the sensory information in a simply reactive way and not in a predictive way, and on the other hand, it is based on old models of voltage-based stimulation, not providing a correct control of the current when faced to the variable impedance of a subject.

Finally, it delivers the current in a markedly discrete manner without taking advantage of the analogous component of its sensory inputs. In addition, the solution disclosed by that patent is not versatile since it does not offer a method capable of adapting to multiple exercises, not providing a real solution to the problem and not achieving coordinated or natural movements in the patient automatically.

Another document, the patent application WO2015/148184A1, discloses a neuroprosthesis based on inertial sensors assigned to assisting the walking of foot drop patients, although not disclosing a system for using sensory information in an intelligent way, so as to be able to adapt to other exercises. Neither does it provide optimal stimulation control, since the stimulation's activation system described by this document is based on two events of the cycle, the beginning and the end of the foot swing. The activation turns the stimulation on or off in a discrete manner, similar to a switch, similar to what can be observed in FIG. 4.a where a constant amplitude is observed, invariable to the patient's muscle needs in an exercise that always has a dynamic character.

Another document, the patent application WO2015/188889A1, discloses a neuroprosthesis based on inertial sensors assigned to assisting the walking of foot drop patients, although not disclosing a system for using sensory information in an intelligent way, so as to be able to adapt to other functional exercises that may be required in order to provide rehabilitation in all stages. Neither does it provide a predictive control in the stimulation since the stimulation activation system described by this document is based on the reactive use of the information given when a discrete cycle event is activated. The attained optimization is only activated after a threshold, and it is reactive, that is, it uses old data to compensate for a single quality measurement, therefore not achieving coordinated or natural movements in the patient automatically. Finally, it translates into a control that usually gives stimulation similar to FIG. 4.b, discrete but with ramps to cushion the cycle's beginning or end (the ramp is used to increase the comfort of the patient upon the stimulus and is not governed by the optimal amplitude that the muscle needs). On the other hand, the solution proposed in this document limits its usefulness to the specific case of foot drop since it depends on the use of electrode arrays, not providing to the user with relocatable electrodes versatility, and foot drop specific stages in the described method, not allowing for adaptation to other movement patterns.

In summary, the functional electrical stimulation industry currently has the disadvantage of not being able to implement functional electrostimulation massively for a homecare scenario nor would this functional electrical stimulation be adaptive to the users' needs nor to be versatile or cost efficient.

This is mainly due to four factors: low versatility offered by state-of-the-art solutions in terms of their use outside the clinic or hospital given their configuration complexity and poor portability; low or none existent inter-compatibility with existing rehabilitation equipment such as bicycles, rowing, weight supports, etc.; deficiencies of current control topologies based on discrete activations instead of predictive stimulation curves; and finally, high implementation, maintenance and operation costs for the equipment due to many processes not being duly automated.

TECHNICAL PROBLEM SOLUTION

In order to solve the problem, a universal and portable functional electrostimulation system (1) with automatic control based on the integration of real-time information from a plurality of sensing devices (200) automatically achieving coordinated and natural movements in the patient is presented.

BRIEF DESCRIPTION OF THE INVENTION
(BENEFITS)

The present system consists of one or more sensing devices (200), which integrate signaling captured by at least one set of sensors (204) with at least one sensor, linked to a body or a pattern generating segment. which are continuously analyzed by a control method; by one or more electrostimulation devices (100) that stimulates the muscles/nerves adaptively based on the control to generate functional movement; by a computational device (300), for example, a smartphone, allowing to configure the system, visualize the system and to register relevant information, and a remote subsystem (400) further allowing to collect and analyze information from multiple independent systems.

This is a system adapted for the realization of a plurality of activities and motor tasks, and it provides great compatibility with all types of machines. These activities range from simple repetitive exercises such as opening and closing a hand, to more complex tasks such as standing or walking. From the main sensing unit, the continuously preprocessed control signals are sent to the stimulator unit indicating the stimulation curves necessary at each moment for each exercise. For instance, the sensing device can be hand manipulated, placed on the bridge of the foot to detect gait or synchronized with bicycles, arm pedals, elliptical trainers, rowing machines, and other rehabilitation equipment. In each of the cases, the stimulation unit can generate the optimal movements in the user's muscles for its rehabilitation.

It should be noted that one advantage over established solutions is the fact of having a high rate of data recollection and integration, unlike other devices that make a significantly discretized control, which makes the control and output of the present invention to tend to be continuous. This information can also be used to estimate optimal therapies and to adapt automatically over time to each patient evolution.

DESCRIPTION OF THE INVENTION

Figure 1:
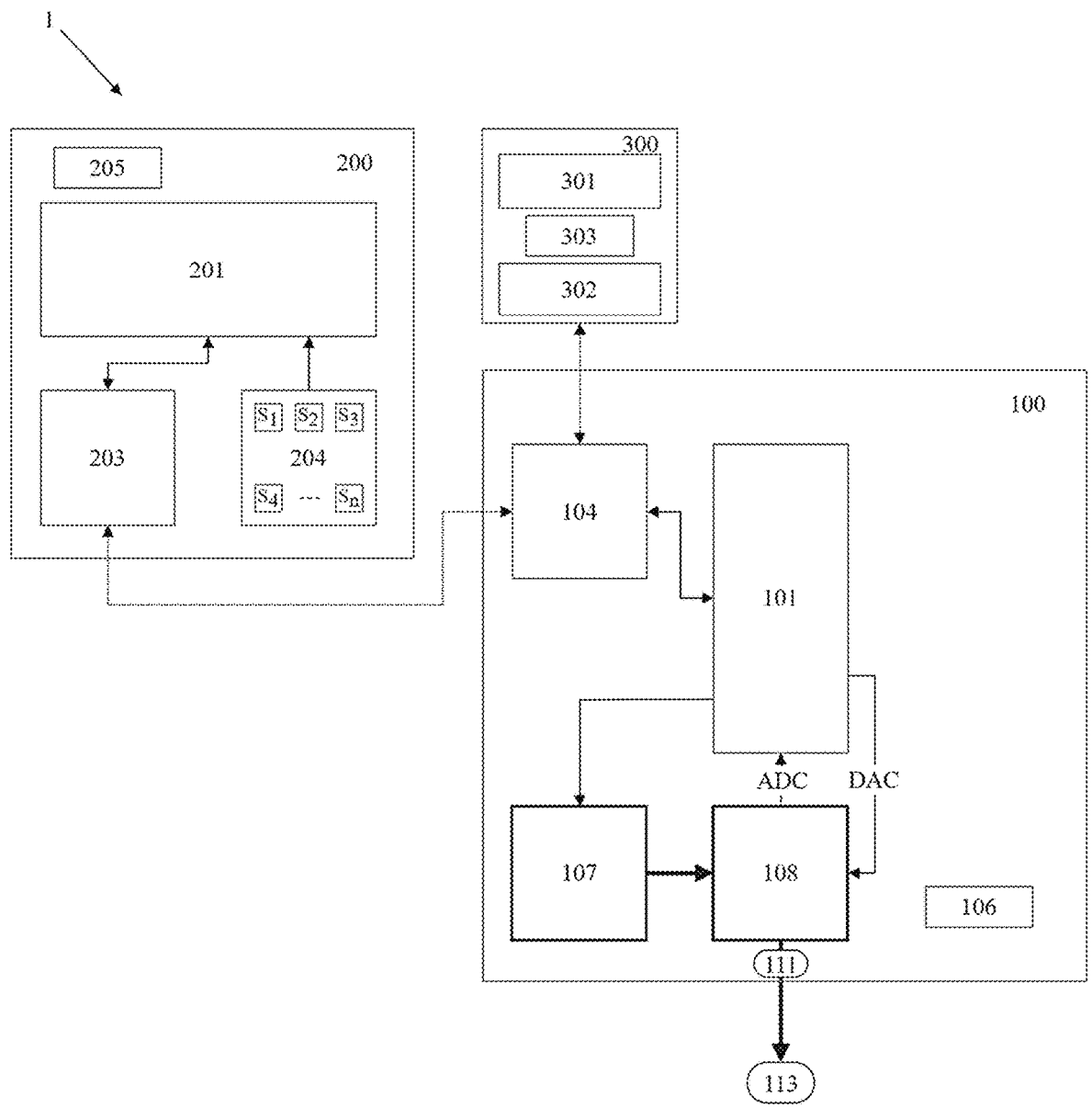
FIG. 1 shows a block diagram representing the system.
Figure 2:
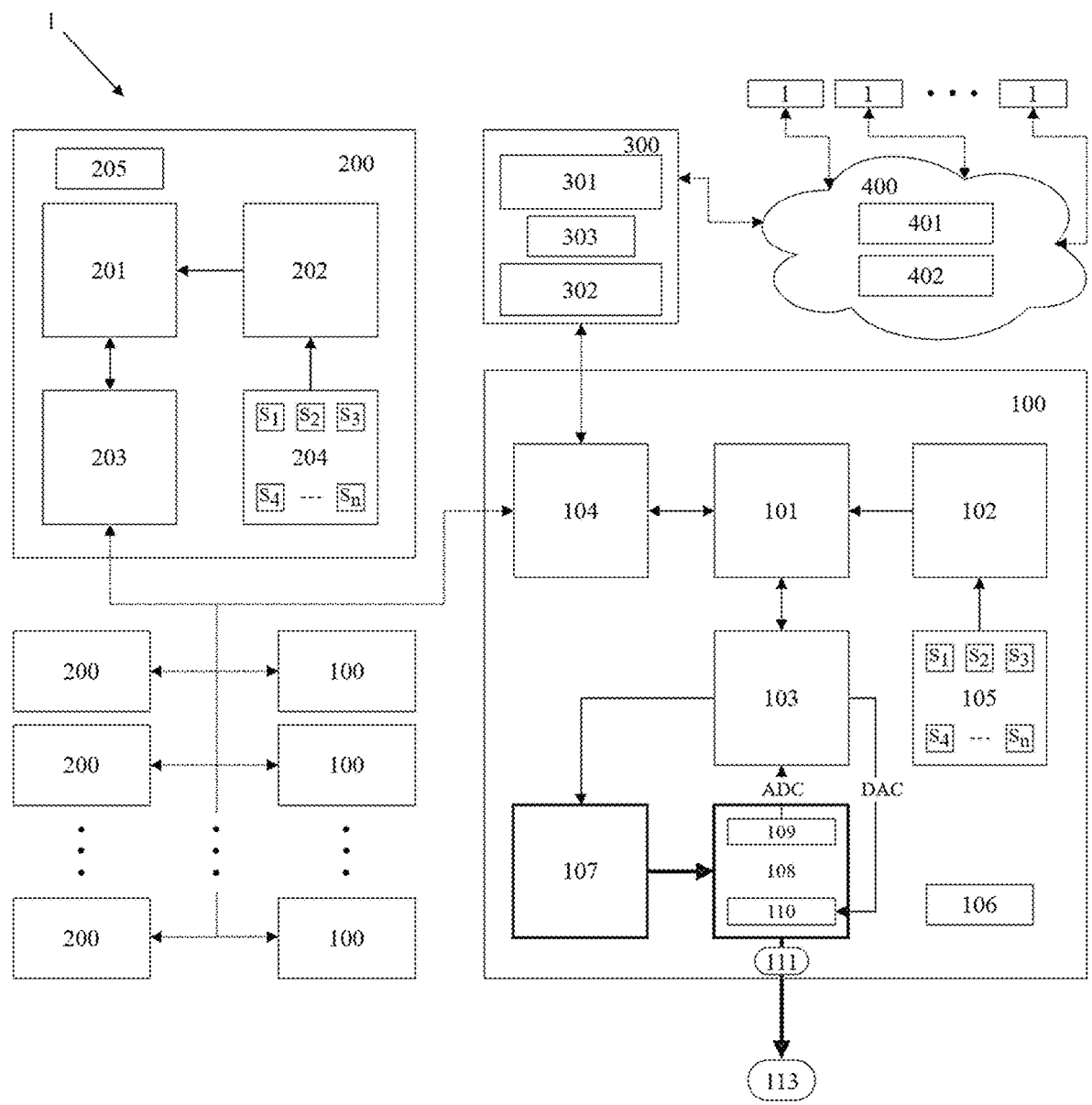
FIG. 2, shows another block diagram representing the system.

As shown in FIG. 1, the present invention consists of a system that includes an electrical stimulation device (100), a sensing device (200), a computational device (300) allowing visualization (301) and configuration (302), a predictive control method and a remote subsystem (400) adding all the information collected by a plurality of these systems, from now on also referred to as the cloud. Other embodiments may incorporate more than one unit of each sensing device (200) and electrical stimulation device (100) as shown in FIG. 2.

Figure 4:
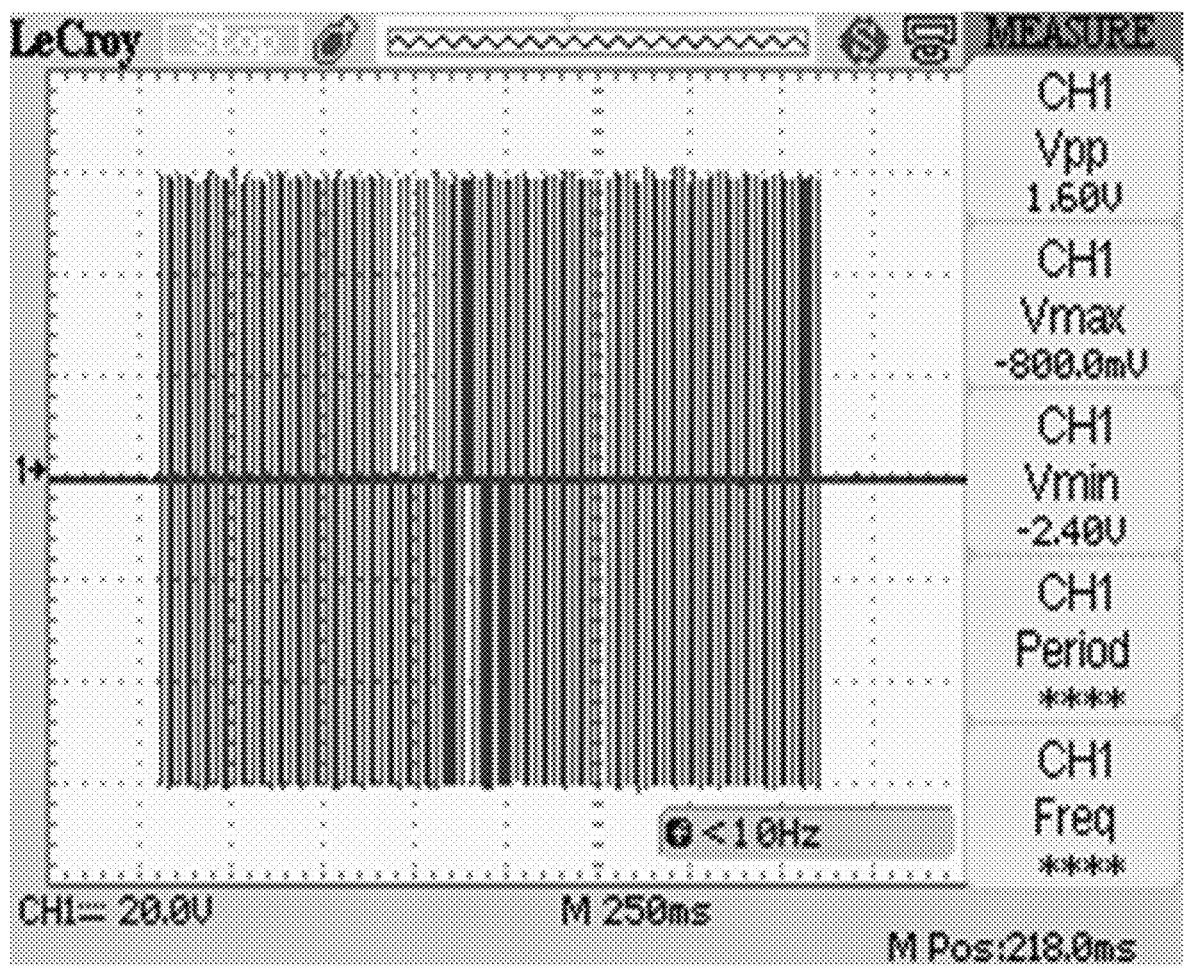
FIG. 4 shows oscilloscope measurements of the current in a stimulation cycle in different cases: a) Traditional stimulation b) Traditional stimulation with ramps c) Stimulation with stimulation curves
Figure 4:
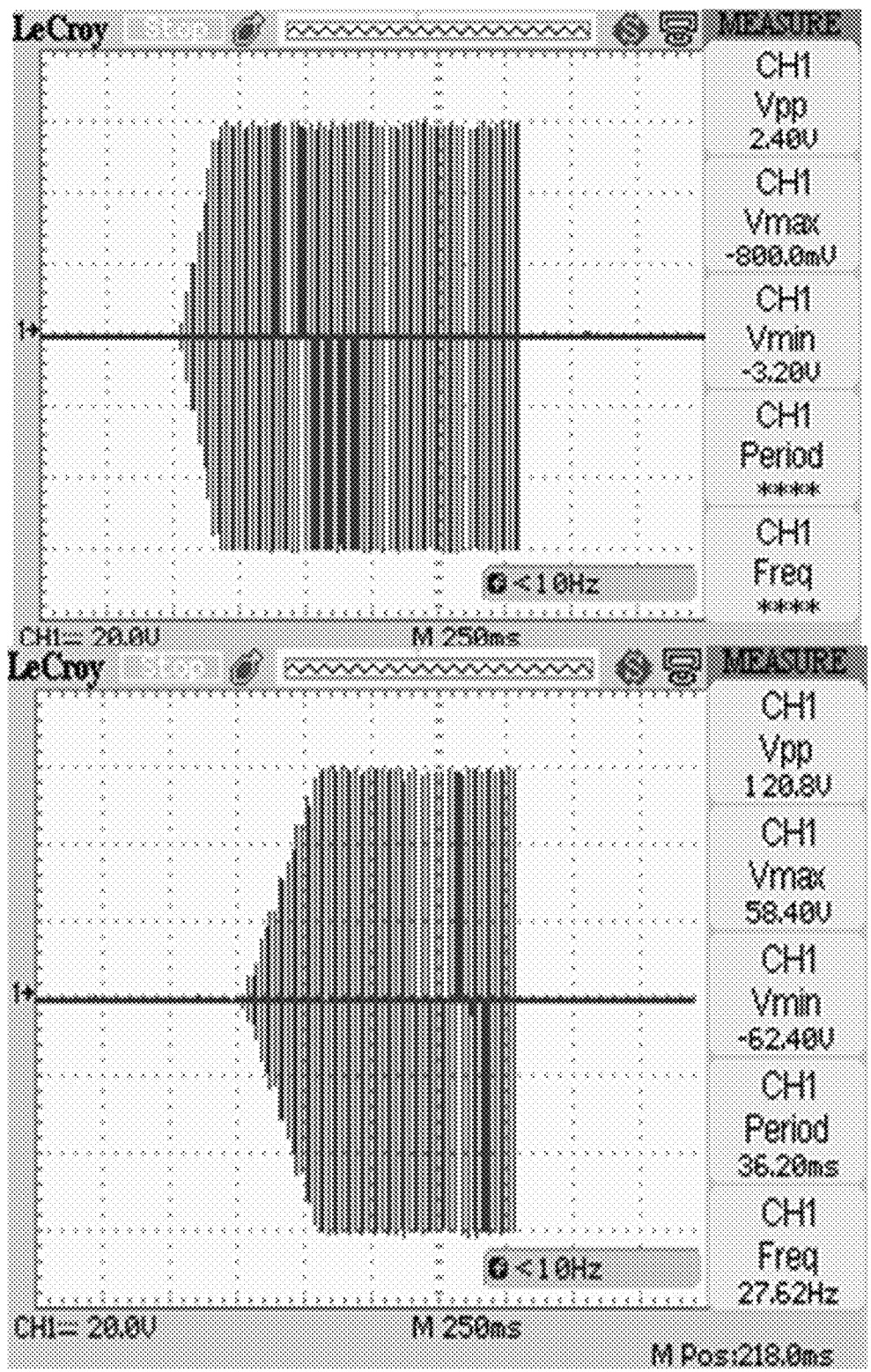
Figure 4:
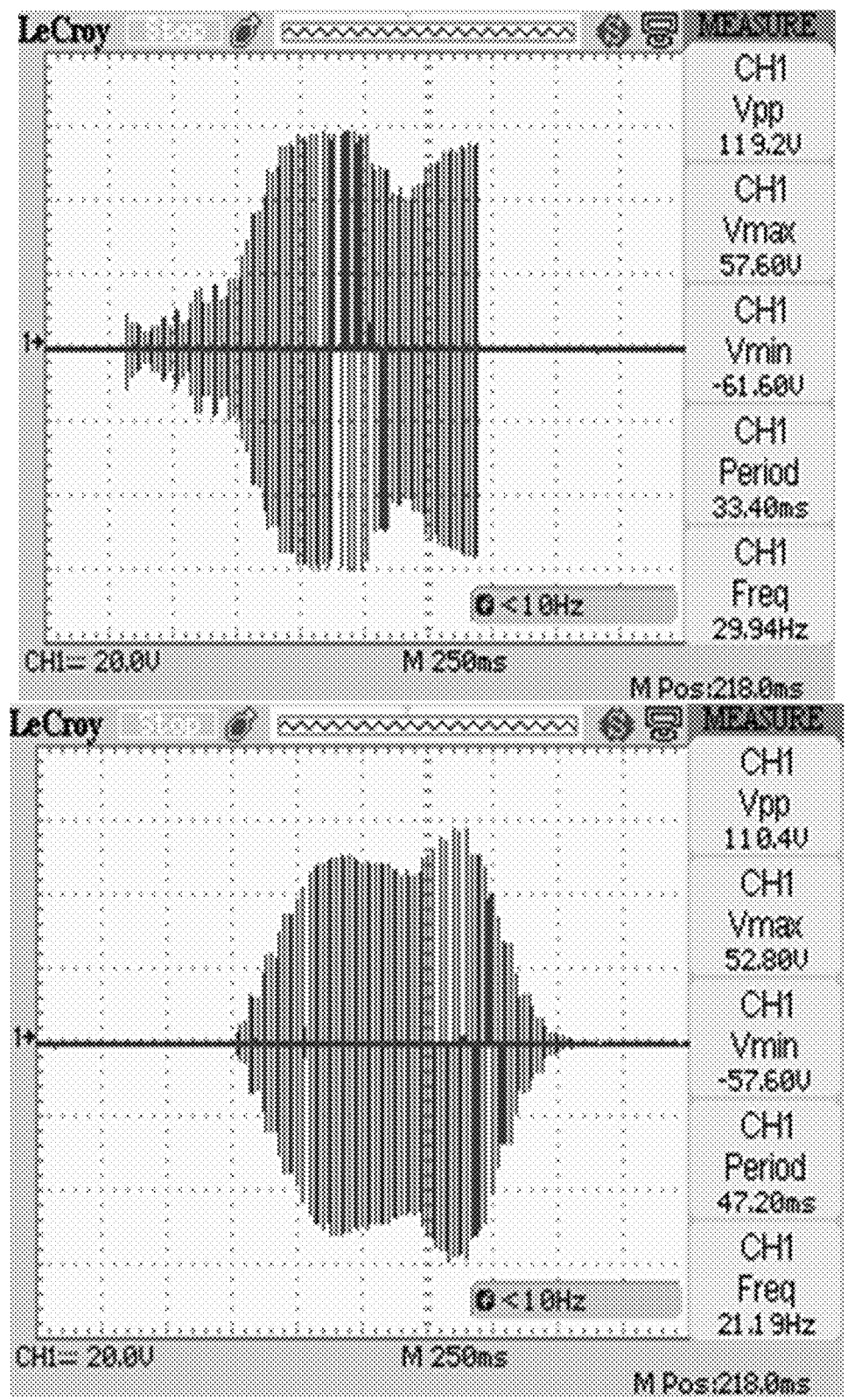

In a preferred embodiment, the electrical stimulation device (100) is capable of generating different stimulation curves. As shown in FIGS. 7a and 7b these curves can have an intensity ranging from 0 mA to equal or over 130 mA. As shown in FIG. 4c, the curves are able to vary their intensity practically continuously, they adapt to the optimum amplitude needed by each muscle of each patient with a refresh rate preferably higher than 50 Hz, but its use can be beneficial from 5 Hz on.

It is appreciated that the approximation achieved by the solutions in FIG. 4a or 4b are rough and lack definition. The varying amplitudes in FIG. 4c reveal that other methods are far from an optimal solution, and that a much finer control is necessary in order to achieve each patient's maximum rehabilitation potential. It can also be appreciated the great variability between one curve and another, demonstrating that this solution must be of dynamic nature to be able to adapt at any time.

Figure 7:
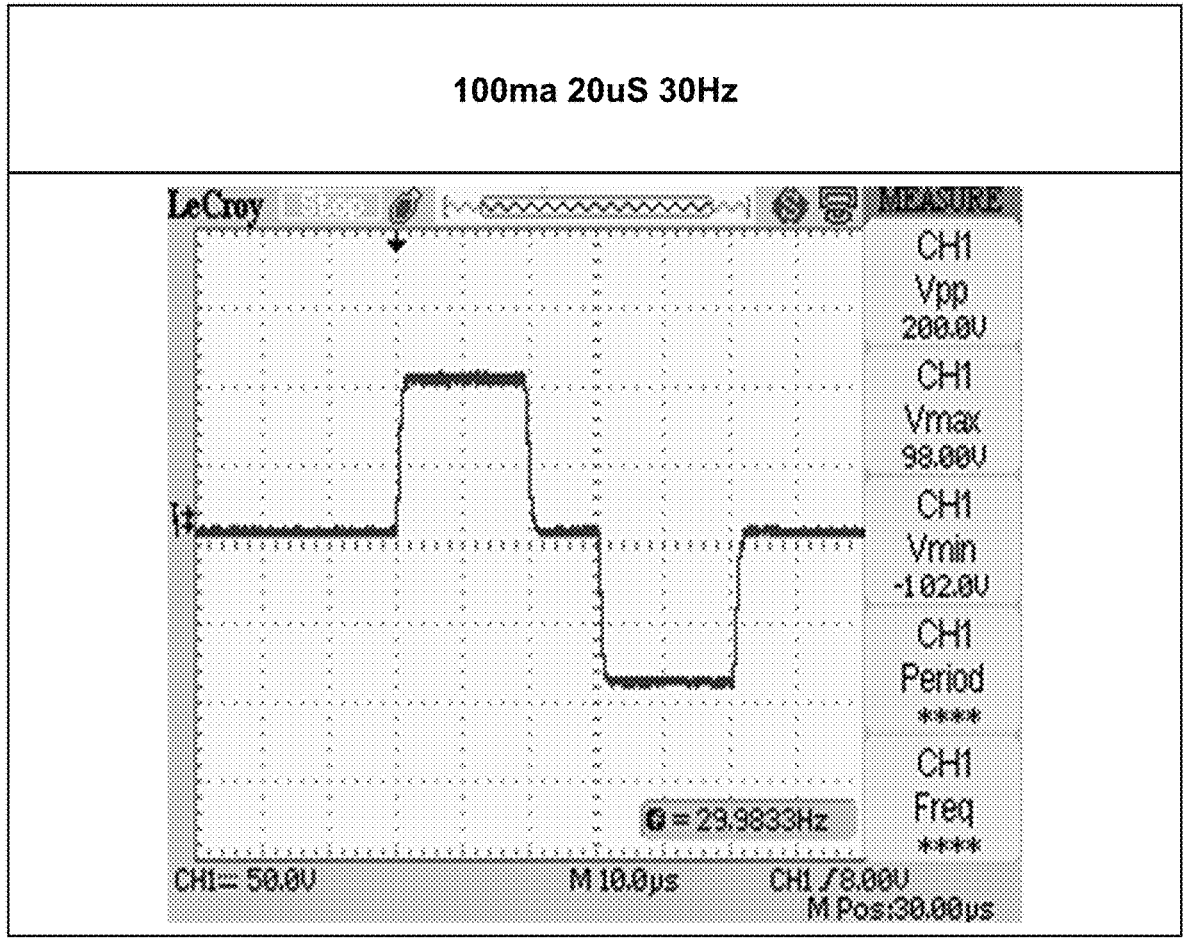
Figure 7:
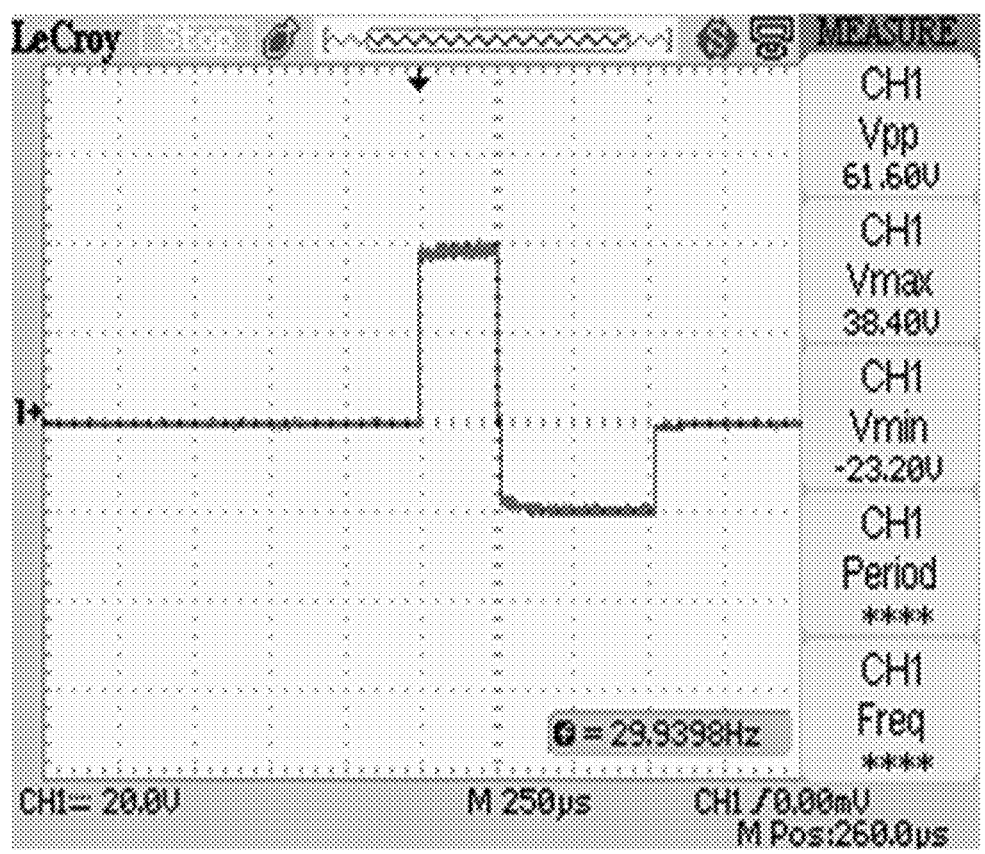

The invention's stimulation curves are preferably composed of stimulation pulses with a width ranging from 0 μs to 400 μs or above, and at a frequency ranging from 1 Hz to 100 Hz or higher. The waveform of these pulses is compensated biphasic square, as shown in FIG. 7. Having a compensated biphasic waveform allows reducing the risk of burns and fatigue since the accumulated potential in muscle cells is zero. A square waveform is used since it delivers more power than a sinusoidal at an equivalent frequency and pulse width. In addition, the stimulator waveform can be symmetric or asymmetric. The symmetric form is the most used by FES systems due to its simplicity. The asymmetric case (FIG. 7b) has the advantage of the muscle acclimatization to the stimulation being less, which allows for a better stimulation for extended periods of time.

Figure 9:
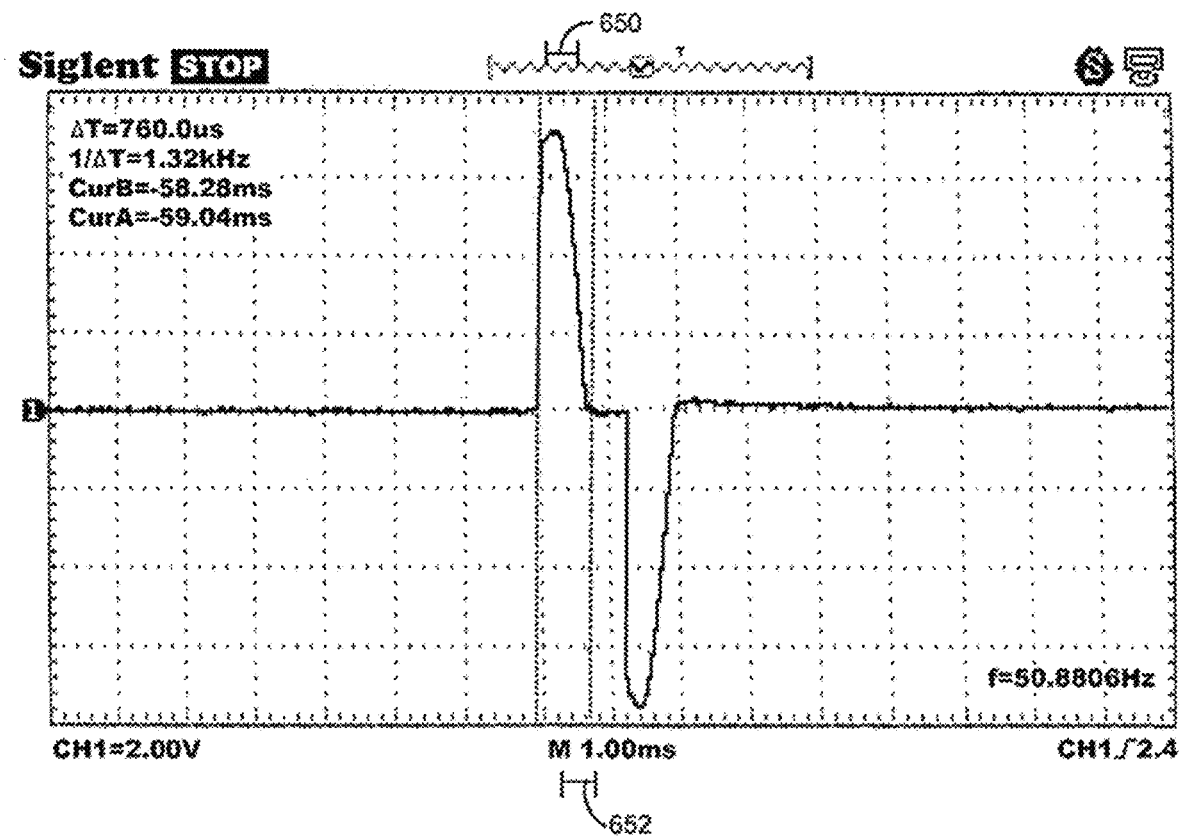
FIG. 9, Corresponds to prior art, corresponding to FIG. 10 of the US20150100107A1 application

Each stimulation curve can contain hundreds of pulses with different amplitudes and widths. In order to achieve greater security and deliver the optimum potential it is important that the invention comprises a pure signal that successfully compensates for the positive and negative phases, and that has a clean stimulation signal like the one shown in FIG. 7. In order to achieve a pure signal, the current controller (108) will preferably sense the current and it will not be a function of the voltage control as in FIG. 10 of US2015 0100107A1. This figure is FIG. 9 of the present application.

As the FIG. 2 detail shows, in a preferred embodiment the current control will be performed in the electrical stimulation device (100) circuit using a current controller (108) comprising a current sensor (109) and a closed loop controller (110) containing active and passive electronic components so as to achieve analogic control. In a preferred embodiment the configuration of the curves followed by the current controller (108) is set by a microcontroller (103), which also allows for other parameters variation in the electrical stimulation device (100) circuit, such as frequency, pulse width and waveform that the high voltage generator (107) will generate. In turn, this microcontroller (103) communicates with the main processor (101) in charge of coordination and communication with the rest of the local functional electrical stimulation system (1).

Another consideration for the safe use of the electrical stimulation device (100) in homecare applications is the automation of security processes. In a preferred embodiment the electrical stimulation device (100) allows the detection of disconnected electrodes (113), stopping the stimulation instantaneously in case of having a positive detection. Other means for interrupting the cycle execution are the emergency stop and the failure of some part of the system. It also allows the independent operation, without communication with other parts of the system. If any part of the functional electrical stimulation system (1) is disconnected, the electrical stimulation device (100) will continue to execute instructions as planned. In addition, it will have anti-spasm control, which allows for reducing spasms while performing an exercise.

Figure 5:
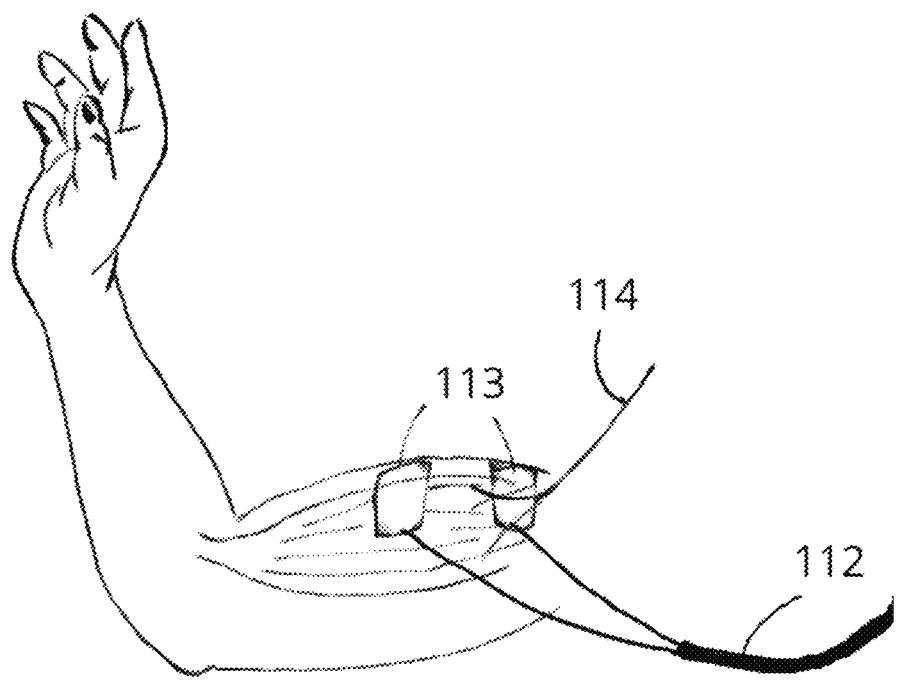
FIG. 5, shows an electrode positioning
FIG. 6, Bicycle connecting rod with sensing device
FIG. 7,
  a) Pulse amplitude ranges
    i 100 mA pulse amplitude, 20 uS pulse width at constant frequency between pulses of 30 Hz
    ii 1 mA pulse amplitude, 400 uS pulse width at constant frequency between pulses of 60 Hz iii 100 mA pulse amplitude, 400 uS pulse width at constant frequency between pulses of 60 Hz b) Compensated asymmetrical pulse FIG. 8, Intensity settings and other electrostimulation parameters.

In a preferred embodiment, the electrical stimulation device (100) has stimulation channels (111) isolated and independent from each other. In one embodiment, there may be 2 stimulation channels (111) acting in different muscle groups. In another embodiment, there may be 6 or more stimulation channels (111) coordinating a plurality of muscle groups. FIG. 5 shows the correct electrodes positioning (113) in a muscle for each stimulation channel (111): the electrode pair (113) is placed in the muscular belly and at the height of the second motor neuron (114), they have no polarity; this electrode pair (113) may be connected by a cable (112) to the corresponding stimulation channel (111) in the electrical stimulation device (100). It should be noted that the position of the muscular belly and second motor neuron varies according to the muscle and according to each user, but the manual positioning adjustment is easy in order to achieve the greatest contraction.

In a preferred embodiment, the electrical stimulation device (100) will have a reduced size and weight, of less than 300 gr, in order to be portable. For instance, in one embodiment it will weight no more than one kilogram, and it will have a volume lesser than about 1 liter. In addition, the device can operate independently of the power line. For instance, by using rechargeable lithium batteries or other types of batteries. To ensure ease of charge, an embodiment of the stimulation device must be capable of raising voltage from 3.0 V (typical minimum voltage of lithium batteries) to 200V or higher. In this way it can make certain that the device is rechargeable with standard connectors such as micro USB (5V), since it would only need one lithium cell.

In a preferred embodiment the electrical stimulation device (100) will have direct communication with the sensing device (200) to get activation instructions, patterns and stimulation curves. In addition, it will communicate with a computational device (300) allowing external configuration of the electrostimulation parameters. This connection will preferably be wireless using means for radio or wireless connection, with frequency orders between 1.8 GHz and 6 GHz, and more specifically between 2.1 GHz and 3.6 GHz, such as Bluetooth® and a microcontroller in charge of the communication. The connection must allow data transmission at a rate equal to or greater than that necessary for the correct communication between the parts of the system. For instance, it will allow the transmission of stimulation curves without delay or loss of information. It is also obvious that information compression protocols may be used, but are not required.

In a preferred embodiment the sensing device (200) will have a series of filters for raw information filters captured by one or more triaxial sensors, which may include, but are not limited to, a magnetometer, an accelerometer, a gyroscope. In addition, it can include other sensors that help capture relevant information. The filters will be processed by the main processor (201) and the secondary processor (202).

In an embodiment of the sensing device (200) a first filter will be operated at a rate equal to or greater than 1000 Hz which will deliver the triaxial orientation of the entire sensory unit. In another embodiment, the first filter of the sensory unit will deliver other information relevant to the movement pattern, including information on pressure, blood flow, and temperature, among others.

In a preferred embodiment of the sensing device (200) a second filter will use the information delivered by the first filter to generate a multivariable information vector necessary to determine a movement pattern at a rate equal to or greater than 100 Hz. Each variable in this vector may have a weight factor. For instance, a vector receiving only the triaxial orientation information, with one second cycles and a 100 Hz rate could have the form $v=[v_{j-n} \ldots v_{j-2}, v_{j-1}, v_j]$ for each cycle j, where $v_j=[m_0 \ldots m_{k-1}, m_k \ldots m_K]$, $k \leq K=100$ and $m_k=(\alpha_j x_k + \beta y_k + \gamma_j z_k)$ with $\alpha$, $\beta$ and $\gamma$ being the weight for the values x, y and z.

In an embodiment, the movement pattern to be determined will be the gait pattern generated by an individual, which is unique to that individual and which may be used for the purpose of correcting the gait of said individual.

In a preferred embodiment of the sensing device (200), a third filter will use the movement pattern determined by the vector delivered by the second filter to determine necessary stimulation curves in each cycle. These curves will adapt automatically in each cycle and even continuously during the same cycle correcting the movement of the user using a closed loop control. The information collected will be used to generate predictive control.

Figure 3:
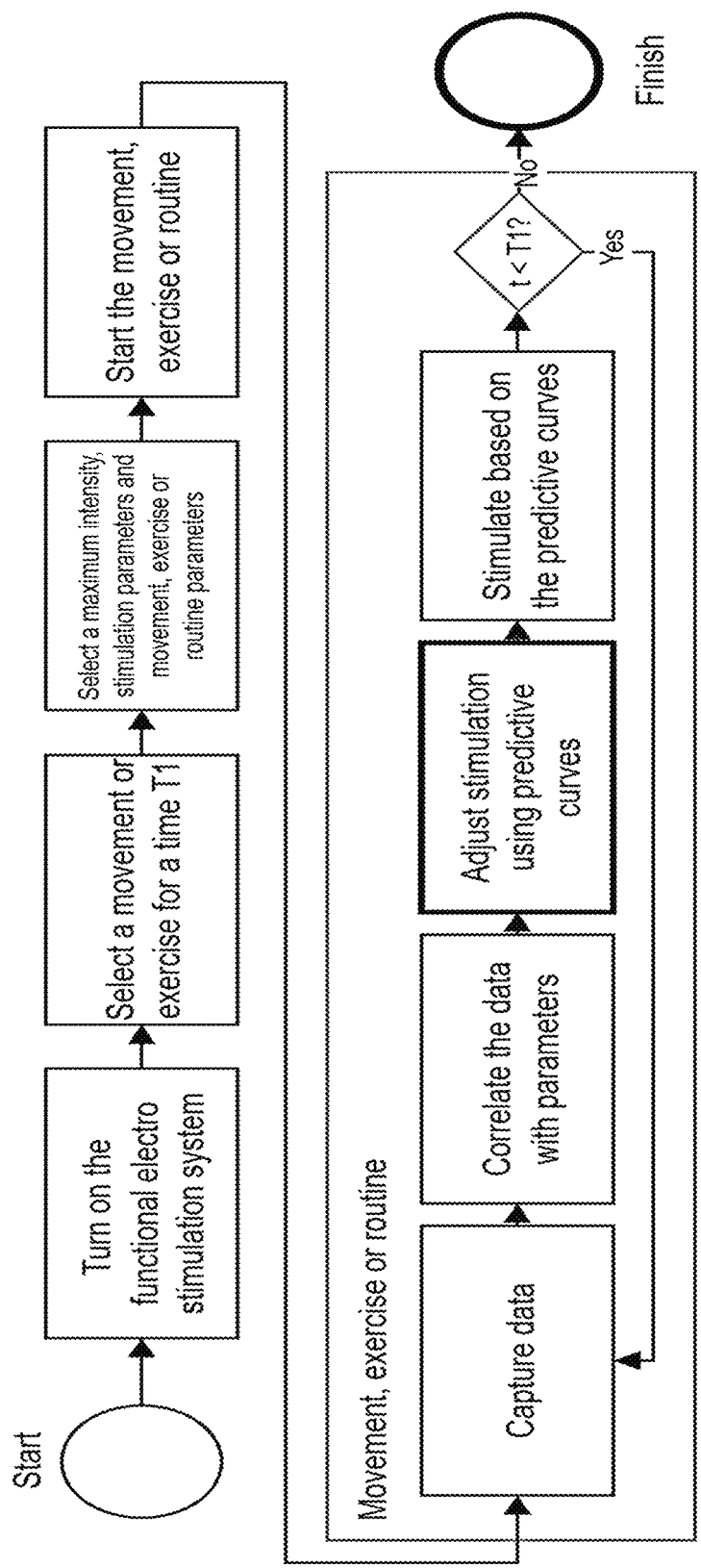
FIG. 3,
  a) Shows a representation of the method's flow
  b) Shows an example of the detail of the control method with filters.
  c) Shows a stimulation curves filter plot
  d) Shows an example of results for the foot drop case
Figure 3:
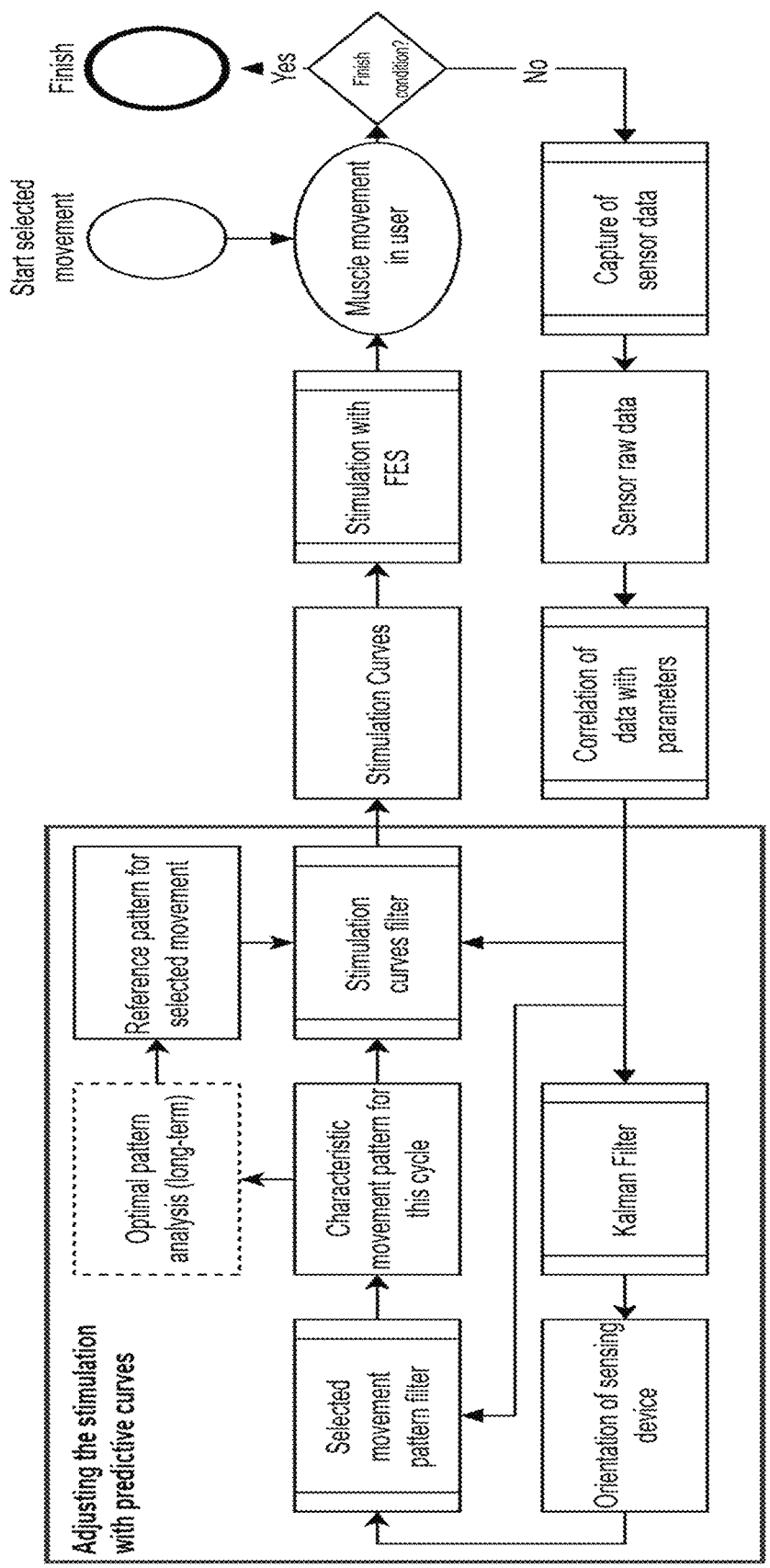
Figure 3:
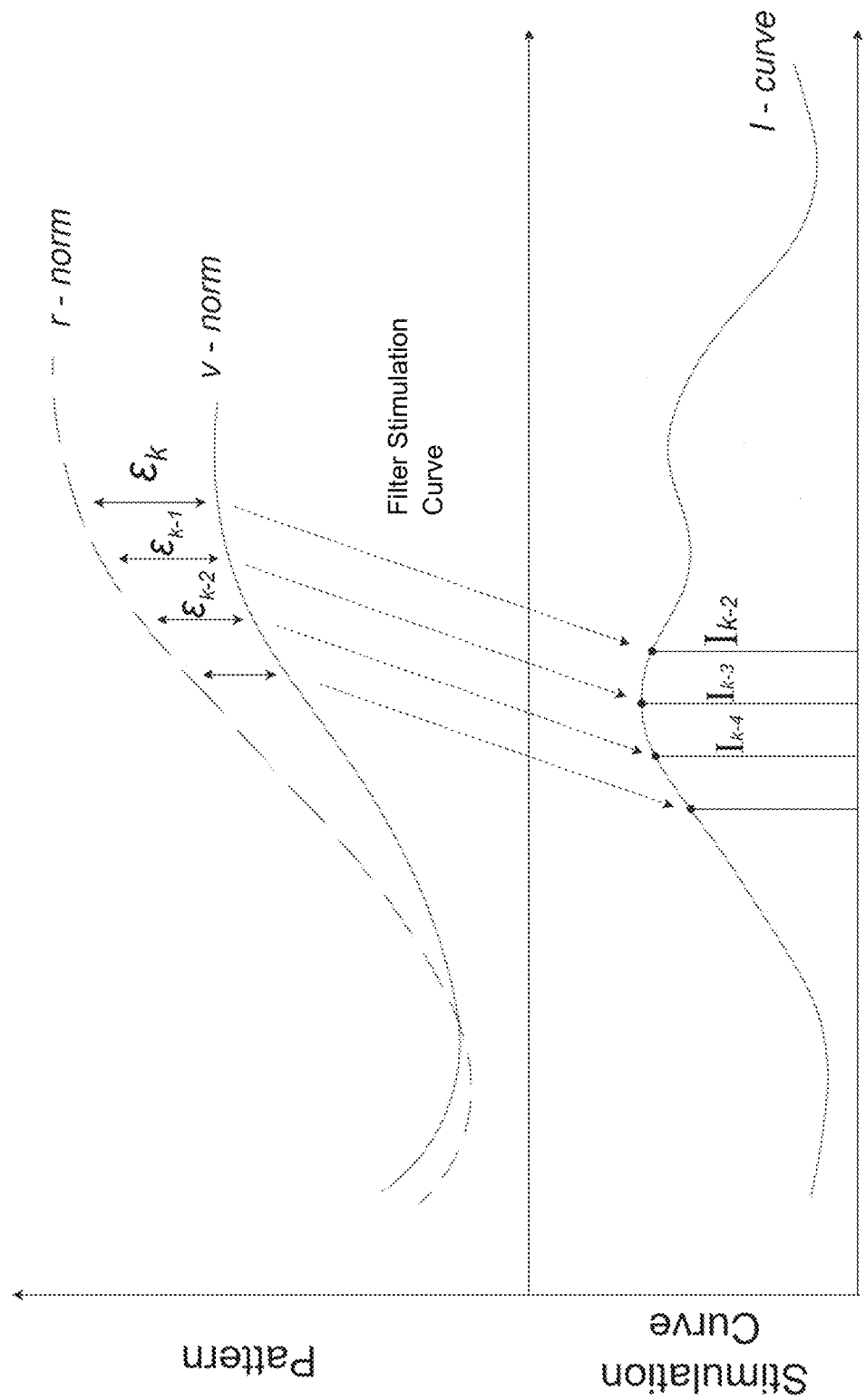
Figure 3:
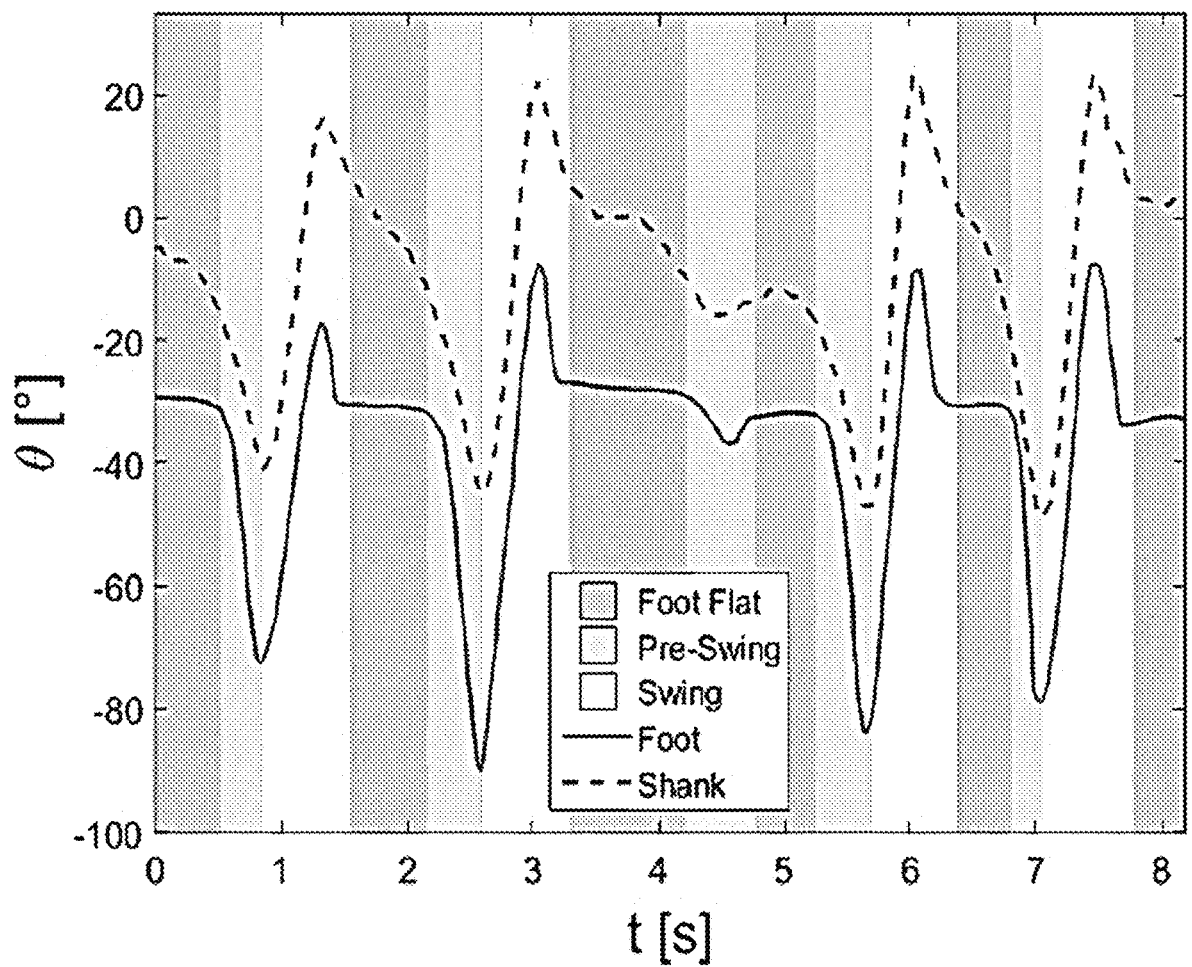

The multivariable vectors that the sensing device (200) captures at each moment with the second filter are weighted according to weights optimized during each cycle and in accordance with the movement pattern type. As shown in FIG. 3b, at the beginning of each cycle they are normalized and temporarily re-sampled for direct comparison with the normalized reference vector r_norm, from which the value $\varepsilon_k$ is obtained for each cycle sample k. Then, a corresponding stochastic intensity $I_k$ is generated in the stimulation curve of each stimulation channel (111), depending on the value of $\varepsilon_k$ and possible being out of phase in time. In addition, this intensity may depend on previous intensities, which may be within or without its own cycle.

In a preferred embodiment of the invention, all filters for determining the stimulation curves will be produced in the sensing device (200). Only in the case of an embodiment having more than one sensing device, it will be necessary to transmit these curves in order to offer autonomy to each sensing device (200). The sensing device (200) is preferably separated from the electrical stimulation device (100), but this may not be the case, that is, it may be embedded in one single unit. It is understood that there is the possibility of making a net or mesh of both sensing devices and stimulators and that these can have any combination of the formats described above, or other formats in other embodiments of the invention.

In a preferred embodiment, the sensing device (200) will have a reduced size and weight, lower than the stimulator, so as to be easy to attach to a segment, body or pattern generating machine. For instance, in one embodiment, it will not have a weight greater than 100 grams or a volume greater than approximately 100 cm$^3$. In addition, the device can operate independently from the power line. For instance, by using rechargeable lithium batteries or other types of batteries. For increased interoperability and compatibility with the system devices, the device will be rechargeable according to standards such as micro USB (5V).

In a preferred embodiment, the sensing device (200) will have direct communication with the electrical stimulation device (100) to deliver activation instructions, patterns and stimulation curves and to receive configuration instructions. In addition, it will be possible to communicate with a computational device (300) allowing external configuration to the sensory parameters. This connection is preferably wireless using a radio connecting mean as Bluetooth® using 2.4 GHz and a microcontroller responsible for the communication which may be for instance an ARM Cortex-M0®, having a central 32-bit processor that runs at 24 MHz, volatile memory of 4 kB, non-volatile memory of 32 kB and multiple discrete and analog input and output connections. The connection must allow the data transmission at a rate equal to or greater than that necessary for correct communication between the parts of the system, greater than 100 kbps. For instance, it will allow the transmission of stimulation curves without delay or loss of information. It is also obvious that information compression protocols may be used, but are not required.

In a preferred embodiment the electrostimulation and sensing devices can be packaged in casings of at least one of the following materials: ABS plastic, polycarbonate, aluminum, carbon, aramid, steel, graphene or other material that offers the necessary strength for a portable device.

Figure 8:
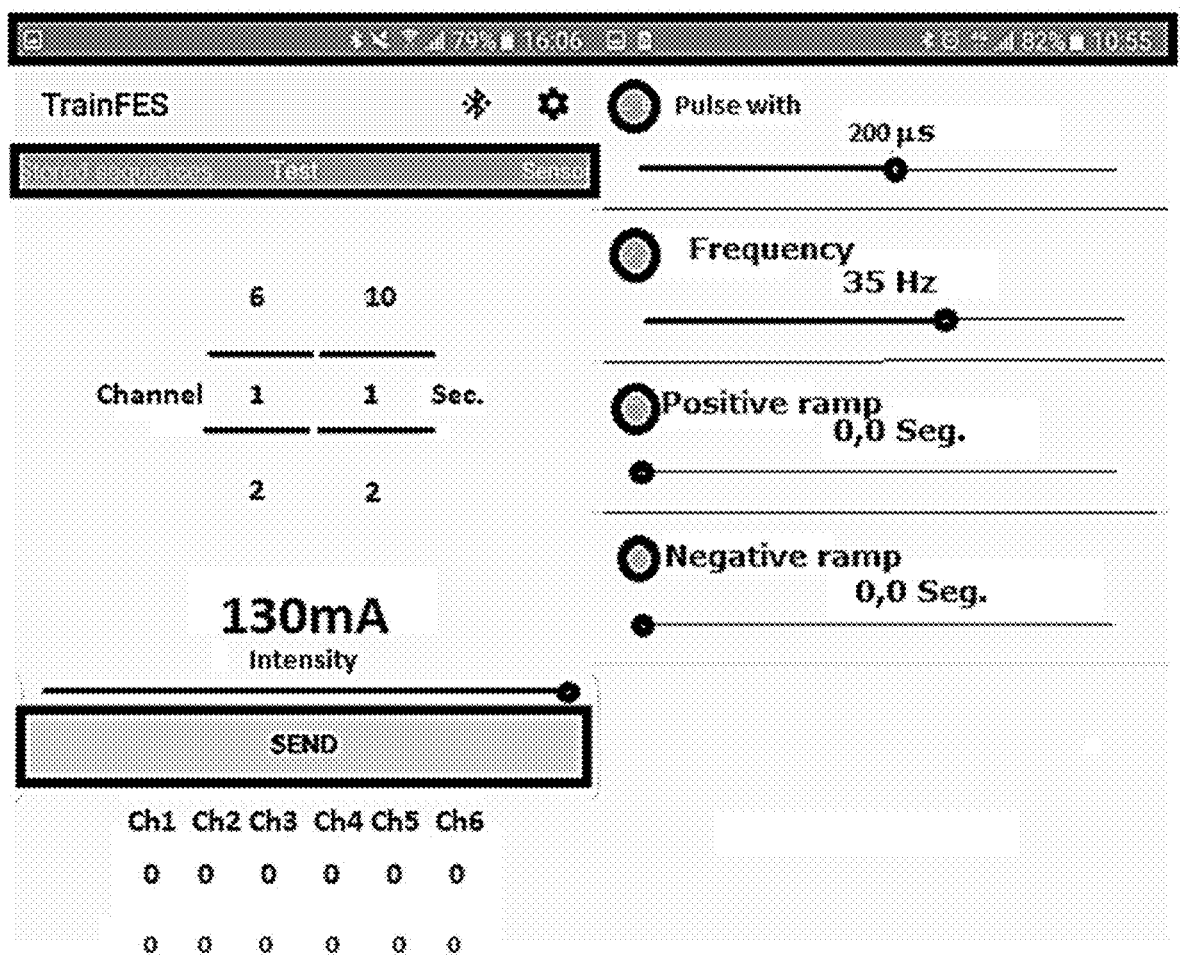

In a preferred embodiment, the invention will have a computational device (300), such as a smartphone, a personal computer, tablet (smartphone, laptop, PDA, etc.) in its system. This device allows sending and receiving information from the electrical stimulation, sensing device or any other device that may be part of the system. The device can be remotely configured or monitor the whole system operation in real time. In addition, it will allow the collection and transmission of information to a remote subsystem (400), storage and information analysis center, or cloud. In another embodiment, this device should not necessarily be proximate to the rest of the system, that is, it can configure parameters remotely. In another embodiment, it will have an interface such as the one seen in FIG. 8.

In a preferred embodiment of the invention, the remote subsystem (400), or cloud, allows synchronization between multiple systems of functional electrostimulation (1) with a local or global database. This subsystem allows remote control of the system's functionalities. In addition, in another embodiment, it adds all the information gathered by multiple systems of functional electrostimulation (1) in a centralized database to generate an intelligent analysis of the collected information. This allows the analysis of large amounts of data, which can consist of system configuration data, system usage data (for instance, results of work sessions), data entered by the user or data identifying the user. With this analysis, independent systems based on big data can be optimized to generate a more natural movement and achieve more effective routines. For instance, it can have optimal reference patterns for each movement type, which are used by the method filters, as shown in FIG. 3a.

In a preferred embodiment, the remote data recollection subsystem (400) or cloud will allow long-term data analysis. In this embodiment, trends can be visualized, warnings can be automated and valuable information can be delivered to each of the users of multiple systems based on an global optimal model, which in turn is based on the high data flow provided by the subsystem and its analysis.

In a preferred embodiment, the user does not necessarily have to be the one occupying the stimulation device. A user can be a patient, a therapist, a clinic manager or another person. In another embodiment there may be more than one user per system.

In a preferred embodiment the invention will have a method for generating control instructions from collected data to achieve coordinated and natural movements based on curves depending on each motor exercise, as shown in FIG. 3a. This method consists in the combination of the filters mentioned above together with the coordinated stimulation (FIG. 3b). The first filter is based on a Kalman filter which has a plurality of integrated triaxial sensors as input data and as output the absolute orientation of the sensing unit (FIG. 3di). The second filter uses orientation through time to kinematically determine movement patterns. For instance, the orientation of the sensing unit in the instep of an individual over time will give the necessary information to determine that individual's walking pattern. Based on the movement pattern generated by the second filter, a third filter can be made to obtain the stimulation curve (FIG. 3c). This curve is dynamic in time and will vary in real time in order to correct the movement the individual wants to make. Following the walking example, the third filter would adapt the stimulation curve according to variations in the walking pattern of the individual in order to correct the gait. In this case the system will try to take the walking as close as possible to the reference at all times in order to generate a closed loop control. As seen in FIG. 3ci, the performance curve control applied to a foot drop patient approaches largely to the reference standard (from a healthy patient).

In a preferred embodiment, the method will allow the use of the system in a plurality of applications. These applications will preferably be motor rehabilitation. Some examples of motor applications include, but are not limited to, standing, walking, rowing, bicycling, foot drop control, mirror therapy, swallowing, strengthening (especially in prostrates), pelvic floor, blood flow control with electronic pump, atrophy prevention in intensive care and treatment.

In a preferred embodiment the method will have an initial manual configuration step for determining parameters. This stage is necessary to ensure user safety and the optimal functioning of the system. Configurable parameters in this step of the method may include mode, intensity, activation angles, frequency, pulse width, symmetry of pulses, cycles or revolutions per minute, ramps, spasms detection, activation times, duty cycles and the total time of exercise T1, among other parameters. By way of example, the intensity must be set by hand each time the system is intended to be used, given the stochastic nature of the muscles behavior. On the other hand, the intensity is also variable according to each person and according to each muscle, independent if it is of the same type or not. The intensity should never generate a contraction producing pain or discomfort in the user. In the case that there is no sensitivity, the user should not administer an intensity greater than that already producing a good contraction due to the risk of producing an injury, such as a tear. Another example is the activation angles, these depend on the selected mode and the articulation range of each user. Other example is the cycle or revolutions per minute, which depend on the force generated by the user and the muscular fatigue generated by generating that force. Other parameters are also of behavior, dependent of external variables that may include time, user, muscle, mode, exercise, fatigue, type of injury and type of exercise machine (if there is one), for which it must be manually compensated in the parameters. Including a manual stage avoids any possible problem that is not easy to detect automatically.

In another embodiment, the method may be automated either partially or completely as the reliability of optimal parameter detection increases.

In another embodiment, external systems to the system of the invention may be used to detect optimal parameters. One of these external systems may be a motion capture system with cameras. Another external system may be an electromyography system. Another external system may be an ultrasonic system.

In a preferred embodiment, based on the chosen parameters and on the user's behavior toward electrostimulation, the system will allow a user behavior analysis in the short and medium term. In one embodiment, the short-term analysis will allow, for instance, to measure the effectiveness of a completed exercise. In another embodiment, the medium-term analysis will allow, for instance, to measure the effectiveness of a series of exercises performed over an extended period. This period can include two or more exercise sessions.

DETAILED DESCRIPTION OF THE INVENTION

According to what is shown in FIGS. 1 and 2, the system of functional electrostimulation (1) allowing to deliver coordinated and natural movements for individuals or animals with damage to the motor system, comprises:
- at least one electrical stimulation device (100) delivering a configurable electrostimulation signal to form dynamic stimulation curves through at least one stimulation channel (111) by means of repositionable electrodes (113) and further comprising at least one main processor (101), which communicates with a communication unit (104), with a high voltage generator (107) and with a current controller (108), which are powered by a first power source (106);
- at least one sensing device (200) bi-directionally connected to the electrical stimulation device (100), wherein the sensing device (200) comprises at least one processor (201), connected to a communication unit (203) and at least one set of independent sensors (204) collecting information, fed by a second power source (205); the sensing device (200) processes and transmits said information to predictively stimulate according to the needs of the user; and
- a computational device (300) bi-directionally connected to the electrical stimulation device (100), wherein the computational device (300) comprises a display screen (301), a configuration unit (302) and a communication unit (303) allowing the exchange of information with the electrical stimulation device (100).

In a preferred configuration, the functional electrostimulation system (1) further comprises a remote subsystem (400) centralizing the information of a plurality of other functional electrostimulation systems (1), wherein the remote subsystem (400), also known as cloud, also comprises a display unit (401) and an analysis unit (402) allowing the analysis of the information of different systems of functional electrostimulation (1) in order to learn and optimize therapies, exercises and routines from each functional electrostimulation system (1) independently.

Communication units (104, 203, 303) are wireless and use radio frequency.

In another preferred configuration, the electrical stimulation device (100) further comprises at least one sensors set (105) containing at least one sensor and a processor (102) for processing and communicating the processed information to the main processor (101).

Wherein each sensor of each sensors set (105, 204) is one from a list of the following sensors: accelerometer, gyroscope, magnetometer, optical, thermal, pressure, bending, acoustic, galvanic, blood flow, heart rate, radiometer, altimeter, geolocation, among others.

In another preferred configuration, the functional electrostimulation system (1) comprises multiple high-voltage outputs called stimulation channels (111) that can electro stimulate more than one muscle group in a coordinated manner; the generation of movements by dynamic predictive curves is not limited to just one muscle group, since it coordinates a plurality of muscles in a user by using multiple stimulation channels (111) and corresponding pairs of electrodes (113), thereby achieving smoother and more harmonious movements.

The sensing devices (200), the electrical stimulation devices (100) and the computational devices (300) are interchangeable between systems, that is, each device can be incorporated into another system different than the original one and, in addition, it is possible to use multiple electrical stimulation devices (100) and sensing devices (200) in the same functional electro stimulation system (1), in communication with each other.

Wherein, the sensing devices (200) are the ones processing the control method and the electrical stimulation device (100), the sensing device (200) and the computational device (300) can be physically attached.

In another preferred configuration, the electrical stimulation device (100) further comprises a microcontroller (103) allowing the variation of frequency, pulse width and waveform generated by the high voltage generator (107) and the current controller (108) comprising a current sensor (109) and a closed loop controller (110) to provide analogic control.

In addition, the electrodes (113) are connected by a cable (112) to the corresponding stimulation channel (111) in the electrical stimulation device (100).

In another preferred configuration, the sensing device (200) further comprises a secondary processor (202) operating in conjunction with the main processor (201), to decrease the processing times, and further comprises a first filter operating at a rate of at least 1000 Hz, to deliver the triaxial orientation of the sensing device (200).

The above enables the sensing device (200) to deliver information on temperature, pressure and blood flow; and luminosity, together with the movement pattern.

The functional electrostimulation system (1) is attached to a bicycle, stationary bicycle, eccentric bicycles, cyclo-ergometers, rowing apparatus partial weight bearing harness, hand pedals, elliptical apparatus and other machines allowing functional exercise, in order to take data and adapt it, therewith achieving stimulation for a smooth and adaptive movement according with the needs of the user, and the configuration.

As shown in the FIGS. 3a and 3b diagrams, a method of functional electro stimulation allowing to deliver coordinated and natural movements for people or animals with damage to the motor system is presented, comprising the following stages:

Turn on the functional electro stimulation system (1);
Select a movement, exercise or routine for a determined time T1;
Select a maximum intensity, stimulation parameters and movement, exercise or routine parameters;
Start the movement, exercise or routine with the following steps:
   a) Capture at least 20 points of data per second with the sensing device (200)
   b) Correlate the captured data with the maximum intensity, stimulation parameters and movement, exercise or routine parameters, for the stimulation selected in the previous stage.
   c) Adjust stimulation using predictive curves;
   d) Stimulate with the electrical stimulation device (100) based on the predictive curves of electrostimulation.
   e) If within time T1, return to step (a), if the time T1 has expired, finish the movement, exercise or routine.

In a preferred configuration, in each cycle the process of adjusting the stimulation with predictive curves comprises:
   To determine the orientation of each sensing device (200)
   To determine the characteristic pattern of movement of each cycle according to the selected movement
   To determine predictive dynamic stimulation curves based on the characteristic pattern of each cycle and a reference pattern that depends on the selected movement.

In another preferred configuration, this is optimized for the movement of more than one muscle group in a coordinated manner; generation of movements by means of predictive dynamic curves, and it is not limited to just one muscle group, since it coordinates a plurality of muscles in a single user employing multiple stimulation channels (111) and pairs of electrodes (113) corresponding to at least one electrical stimulation device (100), achieving therewith smoother and more harmonic movements.

In another preferred configuration, the information captured by sensors and movement pattern further includes: pressure, temperature, force, blood flow and brightness, among other user measurement variables.

In case of any contingency, the execution of the cycle is interrupted in at least the following cases: emergency stop, disconnected electrodes (113), failure of any part of the system.

The microcontroller (103) of the electrical stimulator device (100) receives the predictive curves and other settings coming from the control method running on the sensing device (200) and thus communicates the instructions, thereby generating and modulating the waves from the high voltage generator (107) and the current controller (108) respectively, in order to achieve with this stimulation a smooth and adaptive movement according to the needs of the user and configuration.

PREFERRED EXEMPLARY EMBODIMENTS

A preferred embodiment of the invention is a system using closed loop control based on motion pattern analysis to generate and correct analog stimulation curves in real time in a plurality of exercises, routines and other cases, in which its use would beneficial for the health of a user suffering paralysis. Different stages of rehabilitation and treatments directly compatible with the invention are shown, while other systems based on FES are only compatible with one or two treatments.

It should be noted that the functionalities described in greater detail below are given as way of example for previously described embodiments, but the functionalities are not just limited thereto. Furthermore, it should be understood that this detailed description only comprises one embodiment and that the invention is capable of having other functionalities, applications and forms of use.

1. In one embodiment, the invention allows the use of functional electrostimulation in the standing of a man with paralysis who suffered a stroke and cannot stand by himself. This person's quadriceps and buttocks are stimulated (other muscle groups to be stimulated may include abdominal muscles, paravertebral muscles). Each independent stimulation channel (111) of the electrical stimulation device (100) will stimulate at least one muscle; stimulation channel (111) 1 is installed by means of electrodes (113) in the right quadriceps, stimulation channel (111) 2 in the left quadriceps, stimulation channel (111) 3 in the right gluteus, stimulation channel (111) 4 in the left gluteus. The maximum intensity, frequency, pulse width and other parameters used for stimulation in each stimulation channel (111) are manually configured from the computational device (300) by the user, for safety reasons. That said, the maximum intensity is usually around 50 mA in this person. With the sensing device (200) in hand, stimulation of the muscles of the person with paralysis is coordinated at the same time as this person tries to stand up, activating quadriceps and buttocks when getting up. The person with paralysis is assisted externally to achieve standing, by another person, a partial weight support, an exoskeleton or by other support means providing stability. He is then assisted with stimulation as he falls back to a base position, in this case sitting.

2. In one embodiment, the invention allows the use of functional electrostimulation with a 37-year-old woman with paralysis while walking. It stimulates the quadriceps, hamstrings, gluteus and tibialis anterior of the person. In addition, it is sometimes necessary to support the walking with additional muscles of the upper extremity stimulation, such as: biceps, triceps or others, and abdominal and paravertebral muscles. Each stimulation channel (111) independent of the electrical stimulation device (100) will stimulate at least one muscle by the use of surface electrodes (113). The odd stimulation channels (111) will go to the right side of the woman and the even to the right. The stimulation channels (111) 1 and 2, 3 and 4, 5 and 6, 7 and 8 will go in quadriceps, glutes, hamstrings and tibialis anterior respectively. On each occasion the maximum intensity, frequency, pulse width and other parameters used for stimulation in each stimulation channel (111) are manually configured from the computational device (300) by the user, for safety reasons. With the use of the sensing device (200), located above the instep of the woman's foot, the woman with paralysis muscle stimulation is coordinated with the cycle and its respective pattern while she is trying to walk. Stimulation curves adapts to the woman's unique walking while she walks, optimizing the assistance offered by electrostimulation.

3. In one embodiment, the invention allows coordinated use of functional electrostimulation in a rowing machine with a 24-year-old man. It stimulates the quadriceps, hamstrings and tibialis anterior of the person. The stimulation channels (111) 1 and 2, 3 and 4, 5 and 6 will go in quadriceps, hamstrings and tibialis anterior respectively. With the use of the sensing device (200) placed below the young man's right leg knee, the stimulation is coordinated while he is trying to paddle. The person with paralysis can be assisted by adaptations in the rowing machine. The stimulation adapts to the rowing extension and flexion cycles, optimizing the assistance given to the man.

Figure 6:
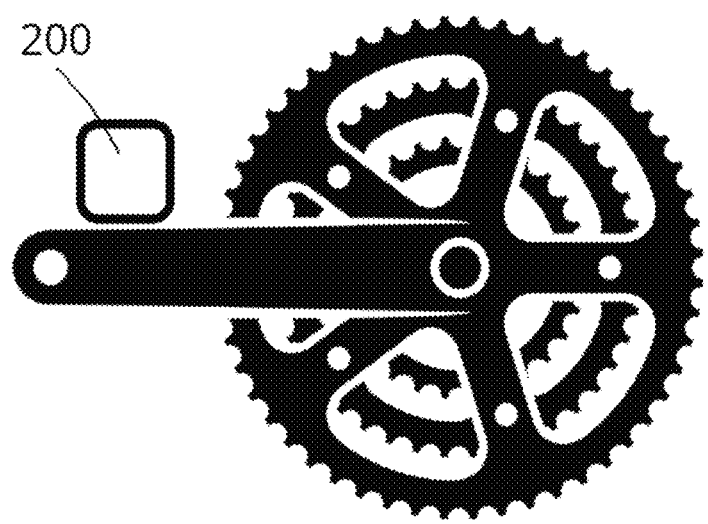

4. In one embodiment the invention allows use of functional electrostimulation in a person with a complete spinal cord injury on bicycles, cyclo-ergometers (active or passive), hand pedals, eccentric bicycles, elliptic and other machine enabling functional exercise by rotation on an axis in order to exercise the lower body muscles and strengthen the upper body. In the case of the lower body, the stimulation channels (111) 1 and 2, 3 and 4, 5 and 6 will go on quadriceps, hamstrings and gastrocnemius respectively. The intensity of the stimulation curves in this case also depends on the revolutions per minute (rpm) that the person achieves in the different machines. In the case of the cyclo-ergometers, the achieved speed is 24 rpm with a 63 mA average intensity, while on the eccentric bicycle it achieves only 16 rpm with a 76 mA average. In the case of the upper body, the hand pedal allows the patient to reach 40 rpm with 20 mA. The sensing device (200) is located in the machine right crank as shown in FIG. 6 for effective coordination of muscle stimulation while pedaling.

5. In one embodiment, the invention allows the use of functional electrostimulation in people with impaired gait, such as drop foot, steppage gait or any other form of impaired walking. For this function it is necessary to stimulate tibialis anterior and further in addition the fibularis, gastrocnemius, quadriceps, hamstrings, gluteus; unilaterally or bilaterally. Other muscle groups to be stimulated may include upper limbs muscles, such as: biceps, triceps or others, as well as abdominal and paravertebral musculature. In the case of a hemiplegic user with drop foot, only one stimulation channel (111) is needed for the tibialis anterior. The invention's daily use will be necessary for this latter case. The maximum intensity of each stimulation channel (111) is manually configured from the computational device (300) by the user each time it is used, since the intensity required for the muscle fibers recruitment can vary from day to day. Using the sensing device (200) placed on the instep of the foot, the tibialis anterior stimulation is coordinated at the same time the individual tries to take a step and walk. The stimulation curves adapt to the cycles of each step and allow correcting the user's gait throughout the day. In addition to the functional electro stimulation system (1), this embodiment of the invention includes as an accessory a Velcro and/or neoprene fastening band located below the knee allowing the attachment of the electrical stimulation device (100) and a hook allowing the attachment of the sensing device (200) to the instep of a shoe or sneaker. The electrical stimulation device (100) is thin enough to be placed under the user's trousers without problems.

6. In one embodiment, the invention allows the use of functional electrostimulation in people having an alteration in an extremity and/or hemibody due to: stroke, brain tumor, brain trauma or neurodegenerative diseases. Furthermore, as with any type of amputation. For this function it is possible to stimulate any muscle or muscle groups. In this case, only one side of the patient will be stimulated and the stimulation channels (111) parity will not be preserved. The movement induced by electrostimulation on the affected side is guided by the movement of the healthy side. That is, if the electrodes (113) are placed in the user's forearm to control his affected hand, the sensory unit must go in the other hand. In this mode a mirror box is used together with the use of the sensing device (200) so the activity the person performs with the healthy limb is reflected on the affected side while the device stimulates the injured limb.

7. In one embodiment the functional electro stimulation system (1) is used in a dog with reduced mobility. The intensity needed in the muscles of the dog is lower than that of a human, close to 15 mA. Electrodes (113) are positioned on the dog hind legs muscles and the movement is assisted with a trolley with wheels. The sensing device (200) is positioned on the dog's right rear leg with a band. The reference movement used is the walking of a healthy dog. The functional electrostimulation allows to increase the dog's articular range during the walking movement and this in turn allows for a faster movement.

To facilitate the reader understanding of the technology, the following list of component parts is presented:

Functional electrostimulation system (1)
Electrical stimulation device (100)
Main processor (101).
Processor (102)
Microcontroller (103)
Communication unit (104)
Sensor set (105)
First power source (106);
High voltage generator (107)
Current controller (108)
Current sensor (109)
Closed loop controller (110)
Stimulation Channel (111)
Cable (112)
Electrodes (113)
Second motor neuron (114),
Sensor Set (105, 204)
Sensing Device (200)
Processor (201)
Secondary Processor (202)
Communication unit (203)
Sensor set (204)
Second power source (205)
Computational device (300)
Display screen (301)
Configuration Unit (302)
Communication unit (303)
Remote subsystem (400)
Display unit (401)
Analysis unit (402)
Communication units (104, 203, 303)

The invention claimed is:

1. A functional electrical stimulation system providing coordinated and natural movements for people or animals with motor system damage, comprising:
at least one electrical stimulation device delivering a configurable electrostimulation signal to form dynamic stimulation curves through at least one stimulation channel by means of repositionable electrodes, and at least one main processor, which communicates with a first communication unit, with a high voltage generator and with a current controller, which are powered by a first power source, wherein the current controller comprises a current sensor and a closed loop controller for obtaining an analogic control;
at least one sensing device bi-directionally connected to the electrical stimulation device, wherein the sensing device comprises at least one processor to a second communication unit and at least one set of independent sensors collecting information, fed by a second power source; the sensing device processes and transmits said information to predictively stimulate according to the user needs;
a computational device bi-directionally connected to the electrical stimulation device, wherein the computational device comprises a display screen, a configuration unit and a third communication unit allowing information exchange with the electrical stimulation device; and
wherein the first, second and third communication units are wireless and use radio frequency.

2. The functional electrostimulation system of claim 1, further comprising a remote subsystem, which centralizes the information of a plurality of other functional electrostimulation systems.

3. The functional electrostimulation system of claim 2, wherein the remote subsystem, also known as cloud, further comprises a display unit and an analysis unit allowing the information analysis of different functional electrostimulation systems to learn and optimize therapies, exercises and routines of each functional electrostimulation system independently.

4. The functional electrostimulation system of claim 1, wherein the electrical stimulation device further comprises at least one sensor set containing at least one sensor and a processor to process and communicate the processed information to the main processor.

5. The functional electrostimulation system of claim 4, wherein each sensor of each sensor set is selected from: accelerometer, gyroscope, magnetometer, optical, thermal, pressure, bending, acoustic, galvanic, blood flow, heartbeat, radiometer, altimeter, or geolocation sensor.

6. The functional electrostimulation system of claim 1, comprising multiple high-voltage outputs called stimulation channels electro stimulating in a coordinated manner more than one muscle group; the generation of movements by predictive dynamic curves is not limited to just one muscle group, but rather it coordinates a plurality of muscles in a user using multiple stimulation channels and corresponding pairs of electrodes.

7. The functional electrostimulation system of claim 1, wherein the sensing devices, electrical stimulation devices and computing devices are interchangeable among systems.

8. The functional electrostimulation system of claim 7, comprising a plurality of electrical stimulation devices and a plurality of sensing devices in a same functional electrostimulation system, communicating with each other.

9. The functional electrostimulation system of claim 1, wherein the sensing devices process the control method.

10. The functional electrostimulation system of claim 1, wherein the electrical stimulation device, the sensing device and the computational device can be physically joined.

11. The functional electrostimulation system of claim 1, wherein the electrical stimulation device further comprises a microcontroller allowing the variation of the frequency, pulse width and waveform generated by the high voltage generator.

12. The functional electrostimulation system of claim 1, wherein the electrodes are connected by a cable to the corresponding stimulation channel in the electrical stimulation device.

13. The functional electrostimulation system of claim 1, wherein the sensor device further comprises a secondary processor operating in conjunction with the main processor, to reduce the time of processing.

14. The functional electrostimulation system of claim 1, wherein the sensor device further comprises a first filter operating at a rate of at least 1000 Hz, to deliver the sensing device triaxial orientation.

15. The functional electrostimulation system of claim 14, wherein the first sensing device filter delivers temperature, pressure, force, blood flow and brightness, together with movement pattern information.

16. The functional electrostimulation system of claim 1, wherein the system is attached to a bicycle, stationary bicycle, eccentric bicycles, cyclo-ergometer, rowing, partial weight bearing harness, hand pedals, elliptical or a functional exercise machine.

17. A method of functional electrostimulation allowing to deliver coordinated and natural movements for individuals or animals with motor system damage using the functional electrostimulation system according to claim 1, comprising:
turning on the functional electrostimulation system according to claim 1;
selecting a movement, exercise or routine for a determined time T1;
selecting a maximum intensity, stimulation parameters and movement, exercise or routine parameters;
starting the movement, exercise or routine characterized by the following steps:
a) capturing at least 20 points of data per second with the sensing device
b) correlating the captured data with the stimulation's maximum intensity, stimulation parameters and parameters for the movement, exercise or routine entered in the previous stage;
c) adjusting stimulation using predictive curves;
d) stimulating with the electrical stimulation device based on the predictive curves of electrostimulation;
e) if within a time T1 then return to step a), if the time T1 has expired, finish the movement, exercise or routine.

18. The method of claim 17, wherein in each cycle, the process of adjusting the stimulation with predictive curves comprises:
determining the orientation of each sensing device;
determining the characteristic each cycle's pattern of movement according to the selected movement;
determining predictive dynamic stimulation curves based on the characteristic pattern of each cycle and a reference pattern that depends on the selected movement.

19. The method of claim 18, wherein the method using the functional electrostimulation system according to claim 1 optimizes the movement of more than one muscle group in a coordinated manner, generates movements by predictive dynamic curves and is not limited to just one muscle group, wherein a plurality of muscles in a user using multiple stimulation channels and pairs of electrodes correspond to at least one electrical stimulation device.

20. The method of claim 18, wherein the captured information from sensors and movement pattern also includes: pressure, temperature, blood flow and brightness.

21. The method of claim 18, wherein the execution of the cycle is interrupted at least in the following cases: emergency stop, disconnected electrodes, failure of any part of the functional electrostimulation system.

* * * * *